Figure 1:
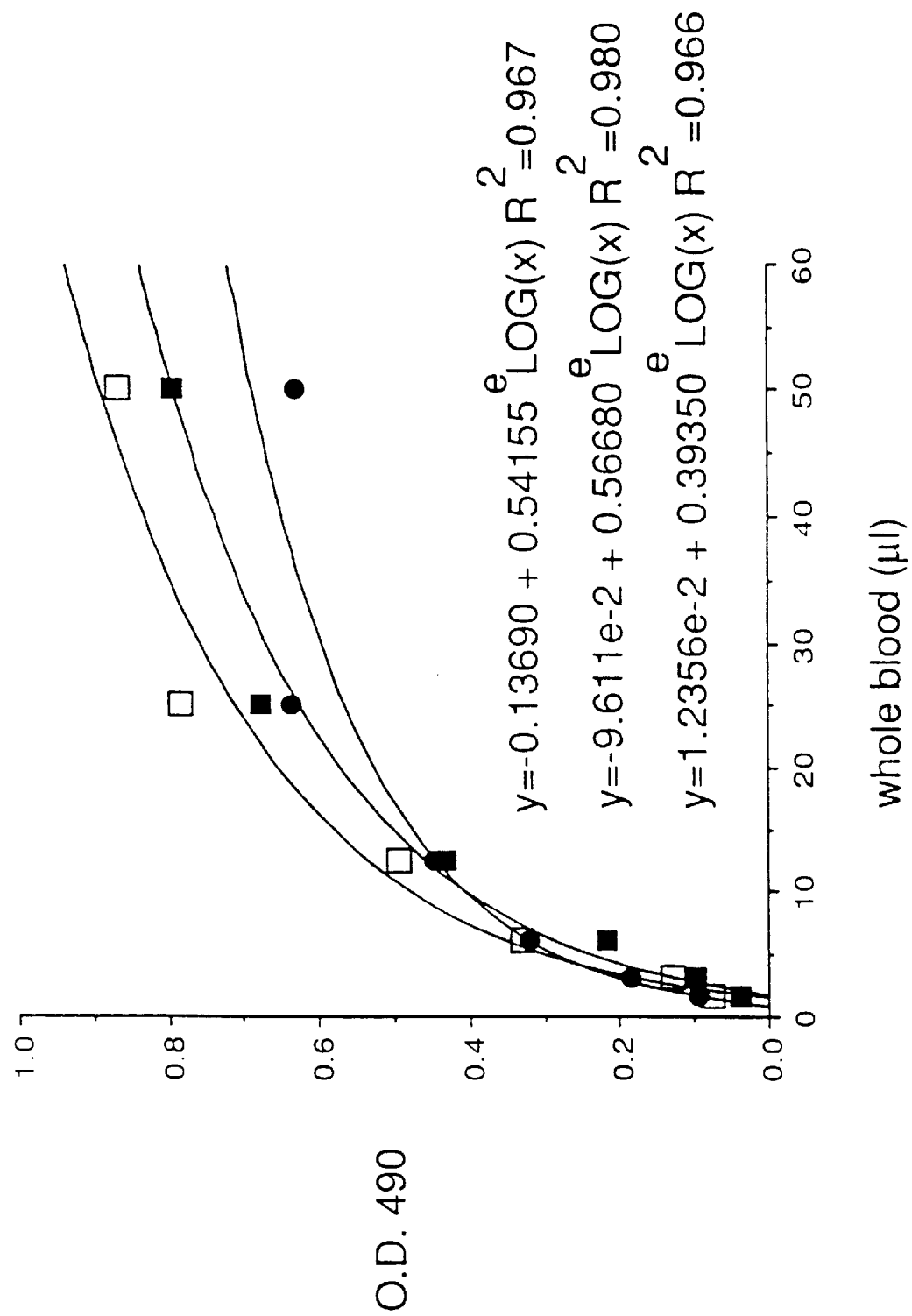

United States Patent [19]

Rittershaus

[11] Patent Number: 5,811,525
[45] Date of Patent: *Sep. 22, 1998

[54] THERAPEUTIC AND DIAGNOSTIC METHODS USING TOTAL LEUKOCYTE SURFACE ANTIGENS

[75] Inventor: Charles W. Rittershaus, Malden, Mass.

[73] Assignee: T Cell Diagnostics, Inc., Needham, Mass.

[*] Notice: The term of this patent shall not extend beyond the expiration date of Pat. No. 5,525,461.

[21] Appl. No.: 432,322

[22] Filed: May 1, 1995

Related U.S. Application Data

[63] Continuation of Ser. No. 50,387, filed as PCT/US91/08085 Nov. 1, 1991.

[51] Int. Cl.$^6$ .................................................. C07K 16/00
[52] U.S. Cl. ............................... 530/388.22; 530/388.2; 530/388.7; 435/7.1; 435/961; 435/972
[58] Field of Search ................................. 435/5, 7.1, 7.2, 435/7.24, 7.92, 961, 972, 975; 530/387.1, 388.2, 388.22, 388.7

[56] References Cited

U.S. PATENT DOCUMENTS

| | | |
|---|---|---|
| 4,299,916 | 11/1981 | Litman et al. . |
| 4,376,110 | 3/1983 | David et al. . |
| 4,391,904 | 7/1983 | Litman et al. . |
| 4,707,443 | 11/1987 | Nelson et al. ............................ 435/7 |
| 4,810,632 | 3/1989 | McMillan .................................. 435/7 |
| 4,845,026 | 7/1989 | Kung et al. . |
| 5,006,459 | 4/1991 | Kung et al. . |
| 5,059,524 | 10/1991 | McKenzie et al. . |
| 5,100,777 | 3/1992 | Chang . |
| 5,503,983 | 4/1996 | Rosoff et al. .......................... 435/7.22 |
| 5,525,461 | 6/1996 | Rittershaus ................................ 435/5 |

OTHER PUBLICATIONS

Ruppert, et al. "IL–4 Decreases the Expression of the Monocyte Differentiation Marker CD14, Paralleled by an Increasing Accessory Potency", Immunobiol. 182:449–464 (1991).

Prince, et al. "Depressed Interleukin 2 Receptor Expression in Acquired Immune Deficiency and Lymphadenopathy Syndromes", J. Immunol. 133:1313–1317 (1984).

Robbins, et al., "Immune Recognition of HLA Molecules Downmodulates CD8 Expression on Cytotoxic T Lymphocytes", J. Exp. Med. 173:221–230 (1991).

Endl et al., "A New ELISA–Based Assay for Quantitation of Human T–Lymphocyte Subpopulations", J. Immunol. Meth. 102:77–83 (1987).

Hessian, et al., Development of an Enzyme Immunoassay for the Quantitation of Cellular Antigen Expression:, J. Immunol. Meth. 91:29–34 (1986).

Morris, et al., "Cellular Enzyme–Linked Immunospecific Assay (CELISA)—A New Micromethod that Detects Antibodies to Cell–Surface Antigens", Human Immunol. 5:1–19 (1982).

*Primary Examiner*—Jeffrey Stucker
*Attorney, Agent, or Firm*—Law Offices of Jane Massey Licata

[57] ABSTRACT

The invention relates to the measurement of total leukocyte antigens, or fragments thereof, and the use of such measurements to enumerate cells, especially in whole blood. The term "total" leukocyte antigen used herein refers to the total amount of a leukocyte antigen in a sample, including that present in membrane and intracellular compartments and extracellular soluble compartments. Measurements of a total leukocyte antigen can be used to type cells, detect or diagnose disease or to monitor disease therapy. In a further embodiment, the invention relates to the measurement of both the amount of total leukocyte antigen and the amount of the soluble form of the leukocyte antigen and a comparison of the measured levels.

5 Claims, 10 Drawing Sheets

THERAPEUTIC AND DIAGNOSTIC METHODS USING TOTAL LEUKOCYTE SURFACE ANTIGENS

This is a continuation of application Ser. No. 08/050,387, filed May 6, 1993 which was a continuation of PCT/US/91/08085 filed on Nov. 1, 1991.

1. INTRODUCTION

The present invention is directed to the measurement of total leukocyte surface antigens, such as T cell receptors and T cell differentiation antigens or fragments thereof, and the application of such measurements in the diagnosis and therapy of diseases and disorders. The present invention is also directed to the measurement of soluble leukocyte antigens or fragments thereof, in conjunction with the measurement of total leukocyte surface antigens and the application of such dual measurements in the diagnosis and therapy of diseases and disorders. The measurement of such molecules, and preferably a plurality of such molecules, can be used in monitoring the effect of a therapeutic treatment, detecting and/or diagnosing disease.

2. BACKGROUND OF THE INVENTION

2.1. LEUKOCYTE SURFACE MOLECULES

Clusters of differentiation (CD) have been established which define human leukocyte differentiation antigens (Bernard and Boumsell, 1984, Hum. Immunol. 11: 1–10; Knapp et al., 1989, Immunol. Today 10: 253: 258; Gebel et al., 1988, ASHI Quarterly 12: 11; Leukocyte Typing III: White Cell Differentiation Antigens. Ed., McMichael, A. J. 1987. Oxford University Press. Oxford), by the comparison of reactivities of monoclonal antibodies directed against the differentiation antigens. The T cell surface antigens, their classification into epitope-defined subgroups, and their distributions on T cells have been studied by use of monoclonal antibodies directed against human T cells (Clark et al., 1983, Immunogenetics 18: 599–615; Hansen et al., 1984, in Leucocyte Typing, Bernard, A., et al., eds., Springer-Verlag, New York, pp. 195–212). Some of the T cell clusters of differentiation and other cell surface molecules are listed in Table I.

These cell surface markers serve as markers of cell lineage, the identity of the functional T cell subset to which the T cell belongs, and the activation state of the T cell. Several of the cell surface molecules have been studied in great detail, have been found to be important in initiating and regulating immune functions and are critical to communication processes between immune cells.

TABLE I
LEUKOCYTE SURFACE MOLECULES

| Cell Surface Marker | Expression | Detection Monoclonal Antibodies | References |
|---|---|---|---|
| T cell Antigen Receptor | All T cells and T cell subsets | T40/251 αF1, βF1, δTCS1, TCRδ1, CγM1 | 1, 2, 3, 4, 5, 6 |

TABLE I-continued
LEUKOCYTE SURFACE MOLECULES

| Cell Surface Marker | Expression | Detection Monoclonal Antibodies | References |
|---|---|---|---|
| CD1 | Thymocytes & Langerhans Calls, Lukemia Cells | OKT6 NAI/34 | |
| NK cell receptor | NK cells | NC-37 specific antibodies | 7 |
| Cell Adhesion Molecules | | | |
| CD2 | All T cells | OKT11 Leu5 B67.1 | 8, 9, 10 |
| CD58 (LFA-3) | Leukocytes, epithelial | TS2/9 | 11 |
| CD3 | Pan T cell | OKT3 Leu4 | 12 |
| CD4 | Helper/Inducer Subsets of T cells | OKT4 Leu3a | 12 |
| CD5 | T.B subsets | UCHT2 T1 | 11 |
| CD7 | T Cells | 3A1 | 11 |
| CD8 | Supressor/ Cytotoxic Subsets of T cells | α Chain: OKT8 Leu2a β Chain: T8/2T8 | 13, 14 14a |
| β2 integrins | | | |
| LeuCAM | leukocyte cell adhesion molecules | | 11 |
| CD11a (LFA-1) | myeloid, lymphoid | | 11, 15 |
| CD11b (MAC-1 (CR3)) | meyloid | | 11, 15, 16, 17, 18, 19 |
| CD11c (CR4) | myeloid | | 11, 15 |
| CD16 (FcR111) | Natural Killer, Macrophages Granulocytes | HUNK2 3G8 | 11 |
| CD21 (CR2) | B subset | B2 HB5 | 11, 20 |
| CD23 (FCεR11) | B subset | MHM6 Blast-2 | 11 |
| CD25 | TAC, IL-2 Receptor (Activated T Cells) | Anti-TAC 7G7/B6 | 21 |
| CD30 | Activated T, B Cells Reed-Steinberg Cells | Ki-1 HSR4 | 11 |
| CD35 (CR1) | Granulocytes, B cells, monocytes | YZ-1 J3D3 | 11, 22 |
| β3 integrins | | | |
| CD41 | | | 11, 23 |
| CDS1 | | | 11, 23 |
| Homing Receptors | | | |
| CD44 | Leukocytes, brain | 33-3B3 | 24 |
| Mel-14 Mel-14 | | GRHL1 | 25, 26 |
| β1 integrins | | | |
| CD49a-f(VLA-1) VLA-2, VLA-3, VLA-4 | Extra cellular Matrix (ECM) | | 27, 23 |

TABLE I-continued

LEUKOCYTE SURFACE MOLECULES

| Cell Surface Marker | Expression | Detection Monoclonal Antibodies | References |
|---|---|---|---|
| CD56 (NKH1, NCAM) | Natural Killer Activated lymphocytes | NKH1 Leu19 | i1 |
| CD71 | Transferring Receptor, Proliferating cells | | 11, 28 |

List of References for Table I.
1. Brenner et al., 1984, J. Exp. Med. 160:541–551.
2. Henry et al., 1989, Hybridoma, 8:577.
3. Brenner et al., 1987, J. Immunol., 138:1502.
4. Wu et al., 1988, J. Immunol., 141:1476.
5. Band et al., 1987, Science 238:682.
6. Hochstenbach et al., 1988, J. Exp. Med. 168:761.
7. Evans, international patent publications #WO89/03394, #WO88/03395, & #WO88/93396 published April 20, 1989
8 Bierer et al., 1989, Annu. Rev. Immunol. 7:579–99.
9. Verbi et al., 1982, Eur. J. Immunol. 12:81–86.
10. Perussia et al., 1983, J. Immunol. 133:180.
11. Knapp et al., 1989, Immunol. Today 10:253.
12. Kung et al., 1979, Science 206:347–349.
13. Reinherz et al., 1979, Proc. Natl. Acad Sci. USA 76:4061–4065.
14. Ledbetter et al., 1981, Monoclonal Antibodies and Tcell Hybridoma, Elsevier, North Holland, N.Y. pp 16–22.
14a. Shieu, L., et al., 1988, J. Exp. Med. 168(6):1993–2005.
15. Kishimoto et al., 1989, Adv. Immunol. 46:149–182.
16. Altieri & Edgington, 1988, J. Biol. Chem 263:7007–1
17. Wright et al., 1988, Proc. Natl. Acad. Sci. USA 85:7734–38.
18. Wright et al., 1989, J. Exp. Med. 169:175–83.
19. Russell & Wright, 1988, J. Exp. Med. 168:279–92.
20. Nemerow et al., 1985, J. Virol. 55:347–351.
21. Uchiyawa et al., 1981, J.Immunol. 126(4):1393–1397.
22. Klickstein et al.; J. Exp. Med. 165:1095–1112.
23. Hemler, 1990, Annu. Rev. Immunol. 8:365–400.
24. Berg et al., 1989, Immunol. Rev. 108:1–18.
25. Lasky et al., 1989, Cell 56:1045–55.
26. Haynes et al., 1989, Immunol. Today 10:423.
27. Hynes, 1987, Cell 48:549.
28. Reinherz et al., 1980, Proc. Natl. Acad. Sci. USA, 77:1588–1592.

2.2. LEUKOCYTE SURFACE MOLECULE SPECIFIC ANTIBODIES

Over the last several years, antibodies to determinants of murine and human TCRs have been developed. Some of these antibodies appear to recognize all members of a V region family, some a subset of V regions within a family, and some a particular V region only (TABLE II). These TCR antibodies identify minor populations of peripheral blood T cells (1–5%) and subdivide T cells in a new way based on TCR V region usage.

TABLE II

| Name | Clone | Specificity | Immunogen | Reactivity | Ref* |
|---|---|---|---|---|---|
| βV5 (a) | 1C1 | Vβ5.2 and Vβ5.3 Subfamilies | HPB | 1–5% of PBL | 1 |
| βV5 (b) | W112 | Vβ5.3 Subfamily subset of βV5 (a) | HPB | 0–3% of PBL | 2 |
| βV8 (a) | 16G8 | Vβ8 family | JURKAT | 1–5% of PBL | 2 |
| βV12 (a) | S511 | Vβ12 family | SEZARY | 1–5% of PBL | 3 |
| βV6 (a) | OT145 | Vβ6 family Allotypic Vβ6.7 epitope | T-CLL | 0–5% of PBL | 4 |
| αV2 (a) | F1 | Vα2 | T-CLL | 1–5% of PBL | 5 |
| αβV (a) | LC4 | Vβ5.1 Subfamily | SUP-T13 | 1–5% of PBL | 6 |

List of References for Table II
1. Boylston et al., 1986, J. Immunol. 137:741–744.
2. Tian et al., 1989, FASEB J. 3:A486 Abstr.
3. Bigler et al., 1983, J. Exp. Med. 158:1000–1005.
4. Posnett et al., 1986, Proc. Natl. Acad. Sci. U.S.A. 83:7888–7892.
5. Janson et al., 1989, Canc. Immunol. Immunother. 28:225–232.
6. Maecker & Levy , 1989, 1989 J. Immunol. 142:1395–1404.

These reagents have proven valuable in studying the repertoire of TCRs expressed under many in vivo and in vitro conditions. For example, in vitro stimulation of mononuclear cells with certain bacterial enterotoxins (superantigens) leads to the expansion of T cells expressing a limited number of TCR Vβ families (Kappler et al., 1989, Science 244: 811–813). In vivo expansion of T cells bearing particular Vβ regions has been detected in certain animal models of autoimmune diseases.

Other antibodies recognize common determinants on all αβ or γε TCRs. These include CγM1, a monoclonal antibody which has been shown to specifically recognize the TCR-γ protein (Hochstenbach et al., 1988, J. Exp. Med. 168: 761). This monoclonal antibody was generated against a constant-region encoded peptide and reacts with both Cγ1 and Cγ2 encoded TCR-γ chains. It appears to possess framework reactivity against all TCR-γ polypeptides.

TCRδ1 (Band et al., 1987, Science 238: 682) and δTCS1 (Wu et al., 1988, J. Immunol. 141: 1476) are monoclonal antibodies specific for the δ chain of the human γδ TCR. Unlike clone specific or idiotypic anti-TCR antibodies, TCRδ1 appears to identify all T cells which express the γδTCR. δTCS1 identifies a minor subset of these γδ T cells.

Additional monoclonal antibodies to the T cell receptor gamma and delta chains have also been reported (European Patent Publication #EP289252 Published Nov. 2, 1988; International Patent Publication #WO88/00209 published Jan. 14, 1988).

βFI (Brenner et al., 1987, J. Immunol. 138: 1502–1509) is a murine monoclonal antibody specific for a framework, i.e., common or nonpolymorphic determinant on the β chain of the αβ TCR and identifies all T cells expressing the αβ TCR. αF1 (Henry et al., 1989, Hybridoma 8: 577) is a monoclonal antibody specific for a framework determinant of the α chain and identifies all T cells expressing the αβ TCR.

Antibodies to CD4 have been widely described (Kung, P. C., et al., 1979, Science 206: 347–349) and are commercially available. A series of such antibodies reacting with non-competing epitopes on the CD4 molecule have been described. Such a set has been termed OKT4, OKT4A, OKT4B, OKT4C, OKT4D, OKT4E, and OKT4F (Rao, P. E., et al., 1983, Cell. Immunol. 80: 310).

Antibodies directed against the CD4 or CD8 antigens have been shown to block cell function. Antibodies against CD4 block most helper T functions, mixed lymphocyte reactions and induction of T helper activity (Biddison et al., 1984, J. Exp. Med. 159: 783). Antibodies against CD8 block the cytotoxic activity of CD8 positive cytotoxic T lymphocytes (Swain, S. L., 1981, Proc. Natl. Acad. Sci. U.S.A. 78: 7101–7105). Antibodies against CD4 have also been described that are capable of activating CD4-positive T cells. CD4 is internalized upon treatment of the cells with phorbol esters and resulting phosphorylation (Hoxie, J. A., et al., 1986, J. Immunol. 137: 1194–1201).

Antibodies to CD35 (Wong et al., 1985, J. Immunol. Methods 82: 303; Yoon & Fearon, 1985, 134: 3332; Schrieber, U.S. Pat. No. 4,672,044 issued Jun. 9, 1987) have also been reported.

2.3. CLINICAL APPLICATIONS

These various lymphocyte cell surface markers have enormous clinical application potentials for the identification of lymphocyte populations and their functional status (Krensky, A. M. and Clayberger, C., 1985, Transplant. 39 (4): 339–348; Kung, P. C., et al., 1984, Monoclonal Antibodies in Clinical Investigations, Clinical Biochemistry-Contemporary Theories and Techniques, Vol. 3, Academic Press, pp. 89–115; Kung, P. C., et al., 1983, Int. J. Dermatol. 22(2): 67–733; Cosimi et al., 1981, N. Engl. J. of Med. 305: 308; Knowles et al., 1983, Diagnostic Immunol. 1: 142; Hoffman, 1984, Amer. Biotechnol. Lab 2: 39).

Existing clinical methods of T cell typing involve the use of monoclonal antibodies which define T cell surface markers to detect the presence of specific cell surface markers on the T cell surface. Measuring the total numbers of T cells expressing a marker on the surface or membrane has been useful for the characterization and classification of lymphoid malignancies (Greaves, M., et al., 1981, Int. J. Immunopharmac. 3(3): 283–300). Changes in the relative percentage of T helper and T suppressor/cytotoxic cells were found to be associated with immune events in renal transplantation due to viral infection (Colvin, R. B., et al., 1981, Proc. 8th Int. Congr. Nephrol., Athens, pp. 990–996), autoimmune diseases (Veys, E. M., et al., 1981, Int. J. Immunopharmac. 3(3): 313–319), and AIDS (Gupta, S., 1986, Clin. Immunol. Immunopathal. 38: 93–100; Ebert, E. C., et al., 1985, Clin. Immunol. Immunopathol. 37-283–297).

The expression of T cell surface markers has also been used for the assessment of the immune status of patients. It has been established that by measuring the relative number of distinct, functional T cell subsets, and/or the relative number of activated T cells in peripheral blood or tissues, an assessment of the immunological condition of a patient is possible.

In an HIV-infected individual, the most useful single prognostic indicator for progression to overt AIDS is the absolute number of $CD4^+$ T cells/$mm^3$ of whole blood. Currently, accurate measurement of $CD4^+$ T cells requires the use of a flow cytometer, both costly and not widely available. In addition, federal guidelines define eligibility for AZT administration to AIDS infected individuals solely on the basis of the $CD4^+$ T cell count (a T cell count which drops below 500 $CD4^+$ T cells/$mm^3$) regardless of symptomology. The cell count cut off for pentamidine treatment is 200 cells/$mm^3$. However, the costly and largely unavailable flow cytometer leaves a large population of clinicians and patients without the means of proper immune status evaluation and therefore AZT treatment.

If the $CD4^+$ T cell count drops below 500 cells/$mm^3$ (AZT treatment) or below 200 cells/$mm^3$ (pentamidine treatment) (Cowley et al, Jun. 25, 1990, Newsweek, pp. 23–27; Mills & Masur, August, 1990, Scientific American, pp. 50–57; Fahey et al., 1990, New Engl. J. Med. 322: 166–72; Goedert et al., 1989, New Engl. J. Med. 321: 1141–8), then the patient is indicated for therapeutic intervention.

The measurement of CD4 positive or CD8 positive T 35 cells may be used to detect or diagnose disease, or monitor disease treatment as described in patents and publications U.S. Pat. No. 4,709,015, U.S. Pat. No. 4,725,543, U.S. Pat. No. 4,361,550, U.S. Pat. No. 4,908,203, W091/10722, W089/08143, W091/07985, EP 421,380, W091/09966, W091/03493, EP 403,935, W088/04327, U.S. Pat. No. 4,695,459, and U.S. Pat. No. 4,649,106.

2.4. METHODS OF MEASURING LEUKOCYTE SURFACE MOLECULES IN A SAMPLE

The methods for detecting, staging or diagnosing a disease, or monitoring the progress of therapy of a disease discussed above require separation of the components of a sample.

For example, methods of diagnosis or monitoring of a patient with a disease may depend on detection of the amount of a soluble leukocyte antigen, and comparison of the amount of soluble leukocyte antigen in the sample from a patient to the amount in a sample from a normal individual or in the same individual at an earlier time. See, e.g., publications WO 87/05912, and WO 90/04180. However, the assay sample must be isolated from cells and cellular debris, which is time consuming.

Prior to the instant invention, measurement of the amount of leukocytes positive for a leukocyte marker was carried out by direct analysis of cells. To date, investigators have primarily measured the amount of cell surface markers in enriched cell populations derived from whole blood. This involved separating whole blood into its serum (or plasma) and cell constituents followed by enrichment of the desired cells by procedures such as those involving the lysis of red blood cells and subsequent isolation of white blood cells on density gradients of polymers, such as Ficoll-Hypaque. The enriched cell populations can then be analyzed either by direct or indirect immunofluorescence involving flow cytometers or fluorescent microscopes, or alternatively lysed with appropriate buffers followed by analysis of either the total lysate or membrane and cytosolic components individually. Limitations of these procedures include (1) the requirement for fresh samples, (2) the need to use enriched cell populations rather than whole blood, (3) the requirements of expensive equipment, (4) the time involved in preparing the samples and (5) the need for fairly large sample sizes or cell numbers for analysis, since cells are lost during the sample preparation steps and because flow cytometric analyses require that a statistically significant number of cells be analyzed for reliable measurements to be obtained. In diseases where the cells of interest are steadily declining, (for example, the decrease in the number of CD4 cells during HIV infection and progression to AIDS) larger sample volumes must be used in order to obtain a significant number of cells to analyze in the enriched cell population.

3. SUMMARY OF THE INVENTION

The present invention overcomes the deficiencies of the prior methods of detecting leukocyte antigens and of estimating the number of cells positive for a particular leukocyte marker by providing a reliable, quantitative, easy-to-use method to measure total amount of a leukocyte marker in a sample containing cells in the biological fluid in which the cells are obtained. Alternately, the sample can contain just cells.

Surprisingly, it has been discovered that treatment of cells in a sample with concentrated detergent followed by dilution of the sample solubilizes the total amount of leukocyte markers in the sample. Thus, the method for determining the total amount of a leukocyte marker in a sample comprises adding a concentrated non-ionic detergent solution to the sample to form a detergent-treated sample, and allowing the detergent to lyse the cells, and/or disrupt membranes. Having released any intracellular and/or membrane bound marker in this manner, the total amount (i.e., inclusive of marker so released as well as any soluble marker that may be present originally in the sample) of leukocyte marker in the sample can be detected. After the cells have been lysed, the sample is diluted to reduce the detergent concentration. Detection of the amount of leukocyte marker in the sample is by immunological detection means, e.g., immunoassay.

Remarkably, measurements of total leukocyte markers can be used to determine the approximate number of leukocytes positive for the leukocyte marker, in a sample i.e., measurement of total leukocyte marker can be used to enumerate cells expressing that antigen with an appropriate correlation. Even more remarkable is the linearity of the correlation between the measurements obtained according to the method of the invention and cell counts achieved by conventional means. Hence, the instant invention represents a highly advantageous substitute for the more cumbersome methods of the prior art.

Measurements of total leukocyte markers are useful in monitoring the effectiveness of a treatment of a subject, in predicting therapeutic outcome or disease prognosis, and in evaluating and monitoring the immune status of patients. Measurements of total leukocyte markers can be accomplished by sandwich enzyme immunoassays where the samples are treated so that the total amount of a leukocyte marker present in membrane, intracytoplasmic and soluble compartments can be measured.

In particular embodiments, the invention is directed to the measurement of amounts of total CD4 antigen. Total CD4 antigen measurements are particularly useful in diseases where the absolute number of CD4$^+$ cells is the best indicator of disease prognosis or, treatment outcome. Such diseases include, but are not limited to, AIDS.

In another embodiment, the invention directed to the measurement of the total amount of CD8 antigen. Total CD8 antigen measurements are especially useful in diseases associated with modulation of the CD8$^+$ subset of leukocytes. These include but are not limited to infectious disease, autoimmune disease, and transplantation rejection illness.

In yet another embodiment, the invention is directed to the measurement of the total amount of T cell antigen receptor (TCR) present in a sample. Total TCR measurements can include the measurement of total TCR on all cells expressing any $\alpha\beta$ or $\gamma\delta$ TCR or can include the measurement of total TCR on particular subsets of cells including, but not limited to, subsets expressing specific $V\alpha$, $V\beta$, $V\gamma$ and/or $V\delta$ peptides.

In a further embodiment, the invention is directed to the measurement of both the amount of total leukocyte marker and the amount of the same soluble leukocyte marker and a comparison of the measured levels. The change in the total levels and soluble levels relative to one another during disease progression or disease treatment can be superior to the measurement of either total or soluble levels alone. Such measurements are useful for the detection, diagnosis or monitoring of treatment of a disease or disorder.

In another embodiment, the invention provides for the measurement of the total amount of two or more leukocyte markers, and comparison of the amounts of the markers. The relative amounts of the markers, or time dependent variation in the relative amounts of the markers during disease progression, can be used to detect, diagnose, or monitor treatment or progress of a disease or disorder significantly, the measurement of total leukocyte markers can be used to estimate the number of cells positive for each marker. The ratios of total leukocyte marker or approximate numbers of cells positive for each leukocyte marker can be compared with the same ratios in a normal individual, and this comparison used to detect, diagnose, or stage a disease or monitor treatment of a disease or disorder.

Simultaneous measurement of the total amount of a marker is an improvement over separately measuring the cell bound, cell lysate or soluble marker for the following reasons. Firstly, the measurement can include the total amount of markers present in all three compartments, not just the amounts present in one or two compartments. Secondly, the measurement of total markers is easier than other procedures that involve greater sample preparation, complex equipment and more steps. Thirdly, small quantities of sample, e.g., 100 $\mu$l, and as little as 5–10 $\mu$l of whole blood, can be directly analyzed in a simple immunoassay format without prior enrichment of the samples. The small volume of whole blood necessary has major benefits in pediatric applications with infants and small children. This represents a significant cost reduction per sample analyzed, and the elimination of an expensive equipment requirement, thereby making the analysis widely available to many laboratories or clinics. Fourthly, the measurement of total marker is an improvement, since it involves minimum sample preparation and does not create aerosols that are hazardous in the case of infectious samples from patients. Most important, for infectious samples such as those containing HIV, the solubilization procedure, i.e., treatment with concentrated detergent, inactivates the virus, thereby making subsequent analysis safer. Fifthly, the total marker assay does not require fresh samples. Each patient sample can be treated and stored frozen. This is especially useful for a series of samples obtained from the same patient over a period of time as in a longitudinal study. Each sample can quickly be treated and frozen so that all samples can be thawed and analyzed simultaneously. This is a definite improvement over flow cytometric analysis where the cells need to be fresh and intact. It also eliminates variance obtained in assay results that arise from interassay variability, since all of the assays may be performed at one time.

3.1. DEFINITIONS

As used herein, the following terms will have the meanings indicated:

| | | |
|---|---|---|
| Total Leukocyte Marker | = | the total amount of a leukocyte antigen or fragment thereof (including membrane-associated, intra- and extracellular) present in a sample. |
| WBCC | = | White blood cell count |
| AZT | = | azido-deoxthymidine |
| HTLV III/LAV/HIV | = | Human T cell Leukemia VIrus Type I/Lymphadenopathy Associated Virus/Human Immunodeficiency Virus |
| OPD | = | O-phenylenediamine |
| mAb | = | monoclonal antibody |
| Spontaneous release | = | release by normal or pathologic physiological processes of the cell |
| AIDS | = | Acquired immunodeficiency disease syndrome |
| TCAR | = | T cell antigen receptor |

5.4. DESCRIPTION OF THE FIGURES

FIG. 1. The measurement of total CD4 antigen in whole blood according to the method of the invention using a CELLFREE® CD4 assay (see Section 5.1, supra). The three curves represent the detection of total CD4 (O.D. 490) from the blood of three normal individuals.

Figure 2:
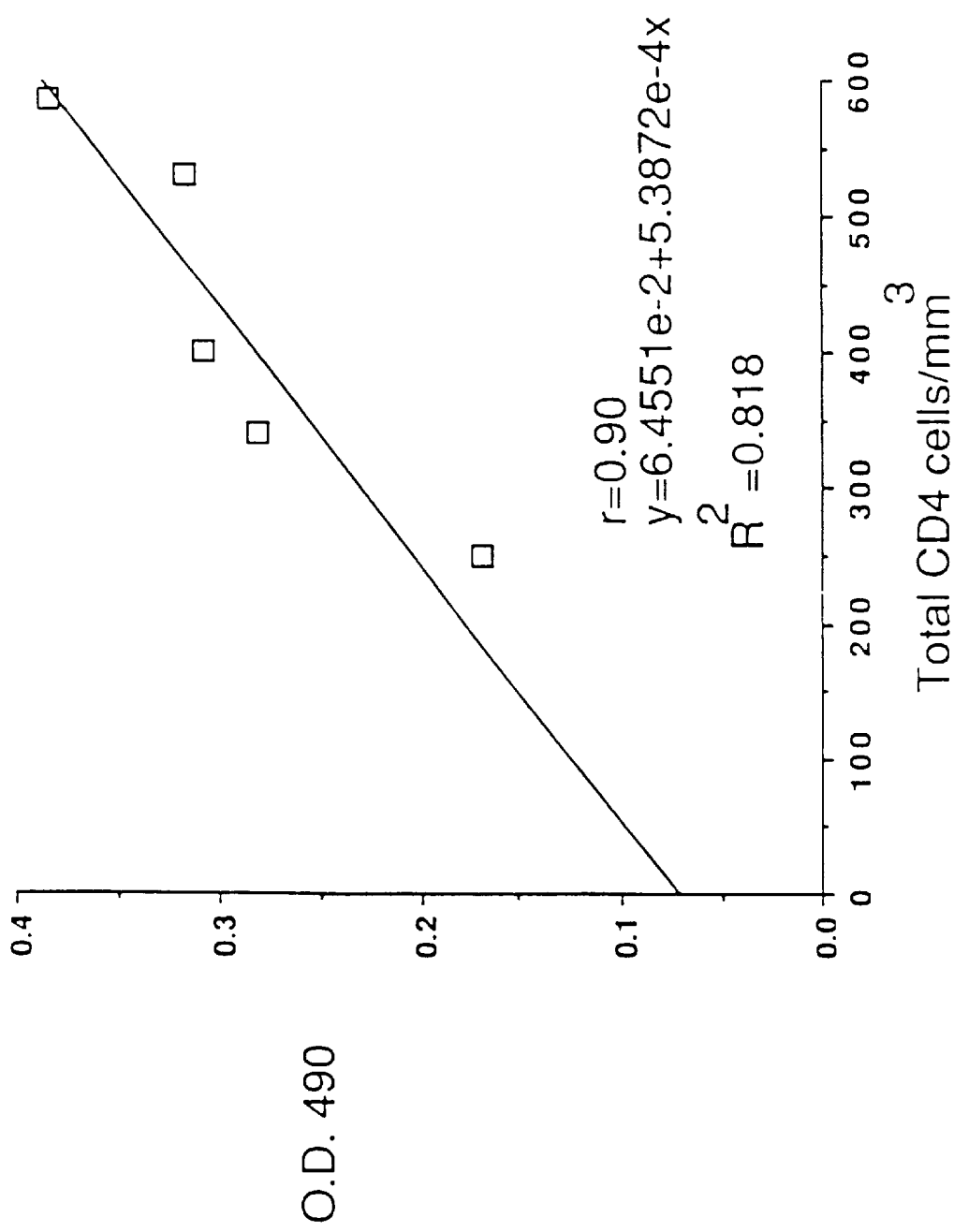

FIG. 2. The correlation between total CD4 antigen as measured in a CD4 immunoassay according to the method of invention and the total number of CD4 positive cells/mm$^3$ of blood. Total CD4 (O.D. 490) was measured from 2.5 μl of whole blood from five different normal individuals using a CELLFREE® CD4 assay. The number of CD4 positive cells/mm$^3$ was measured in the blood samples three days after determination of total CD4 antigen from the samples. Thus, the number of total CD4$^+$ cells/mm$^3$ of blood appear lower than expected for normal individuals. However, the curve obtained shows a linear relationship between total CD4 antigen and the number of CD4+ cells.

Figure 3:
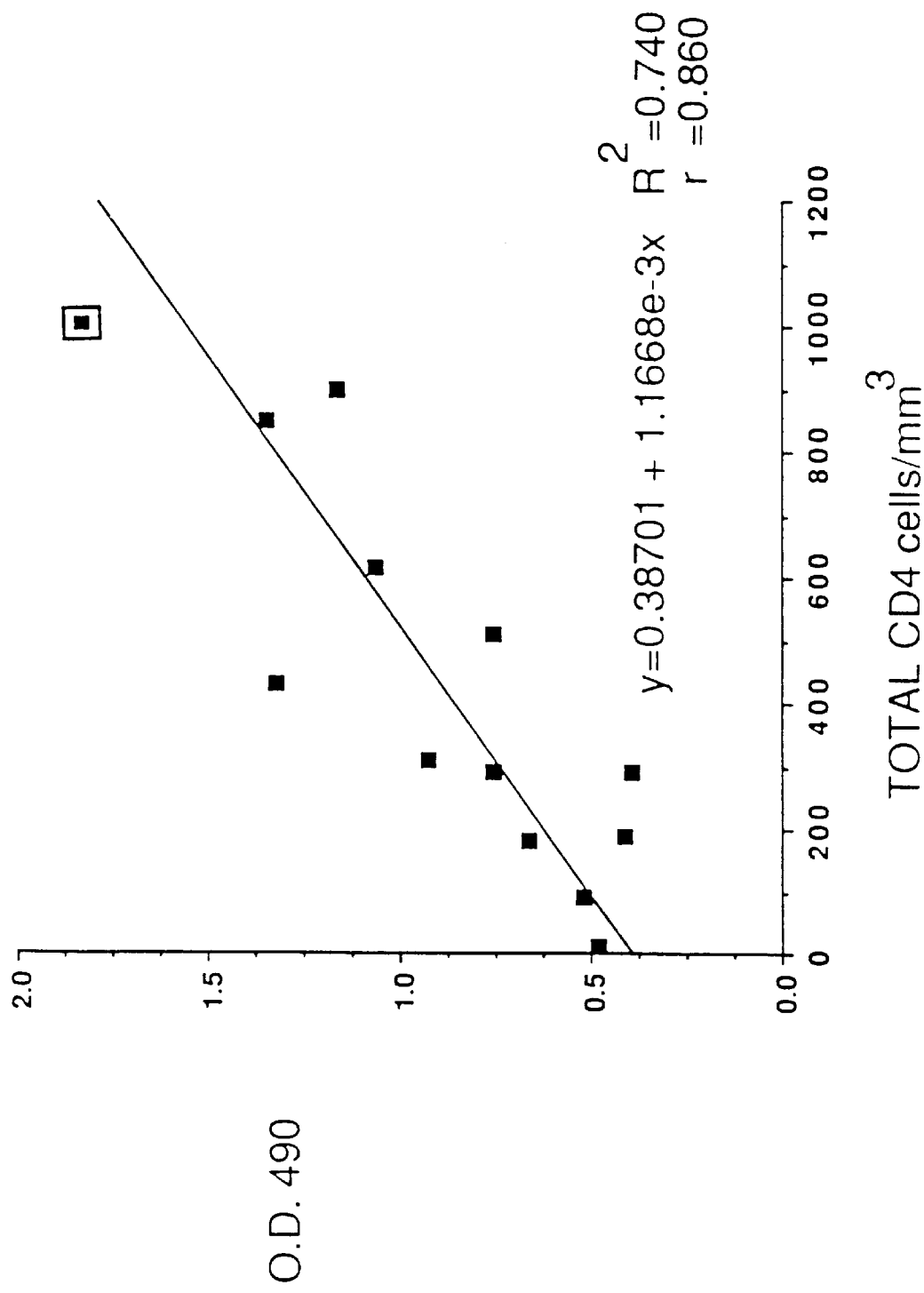

FIG. 3. The correlation between total CD4 antigen measured from whole blood of HIV-infected individuals and one normal control and total CD4$^+$ cells/mm$^3$ of blood. HIV-infected individuals are represented by a single square and the normals by the double square.

Figure 4:
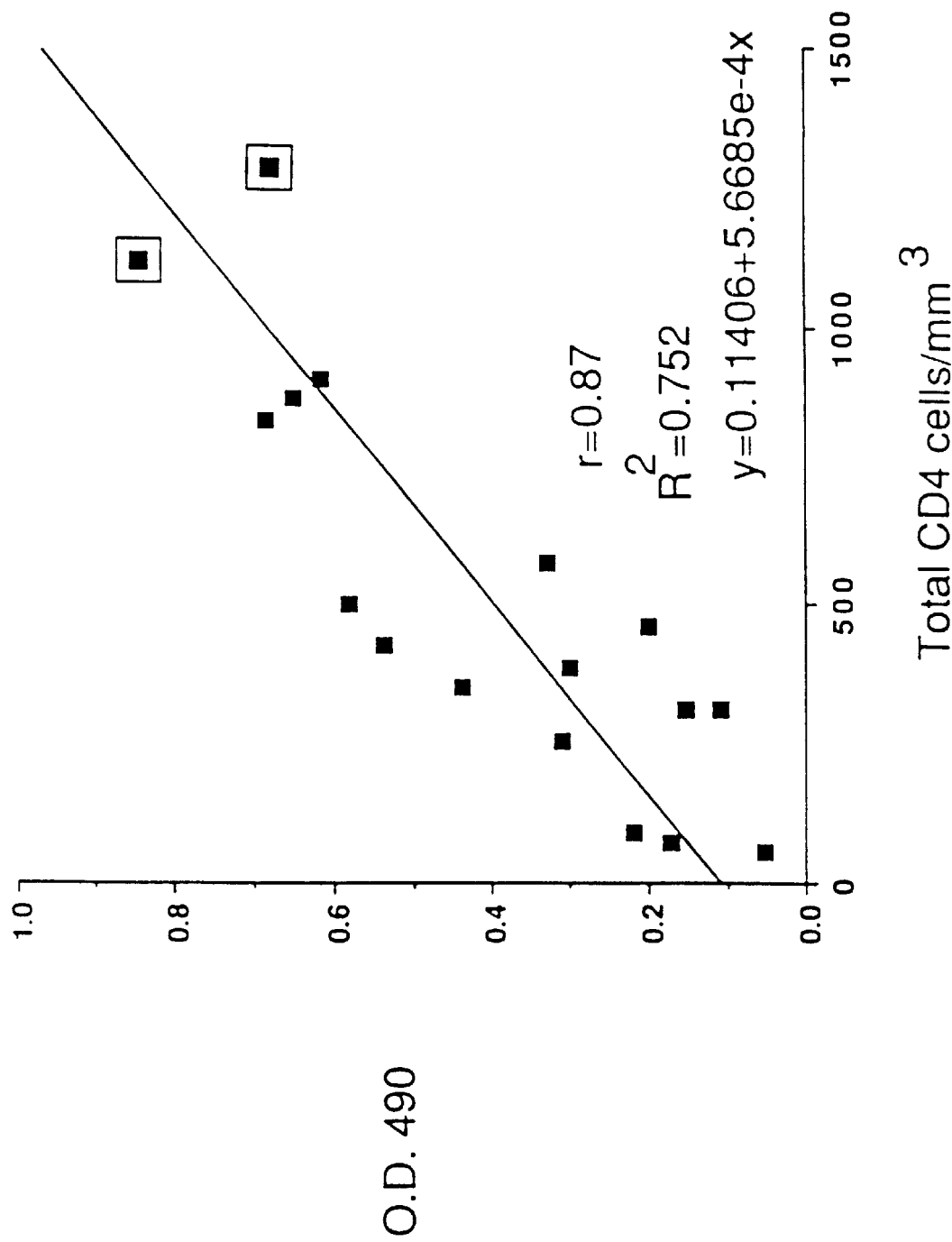

FIG. 4. The correlation between total CD4 antigen measured from whole blood of HIV-infected individuals and normal controls and total CD4$^+$ cells/mm$^3$ of blood. HIV-infected individuals are represented by a single square and the normal by the double squares.

Figure 5:
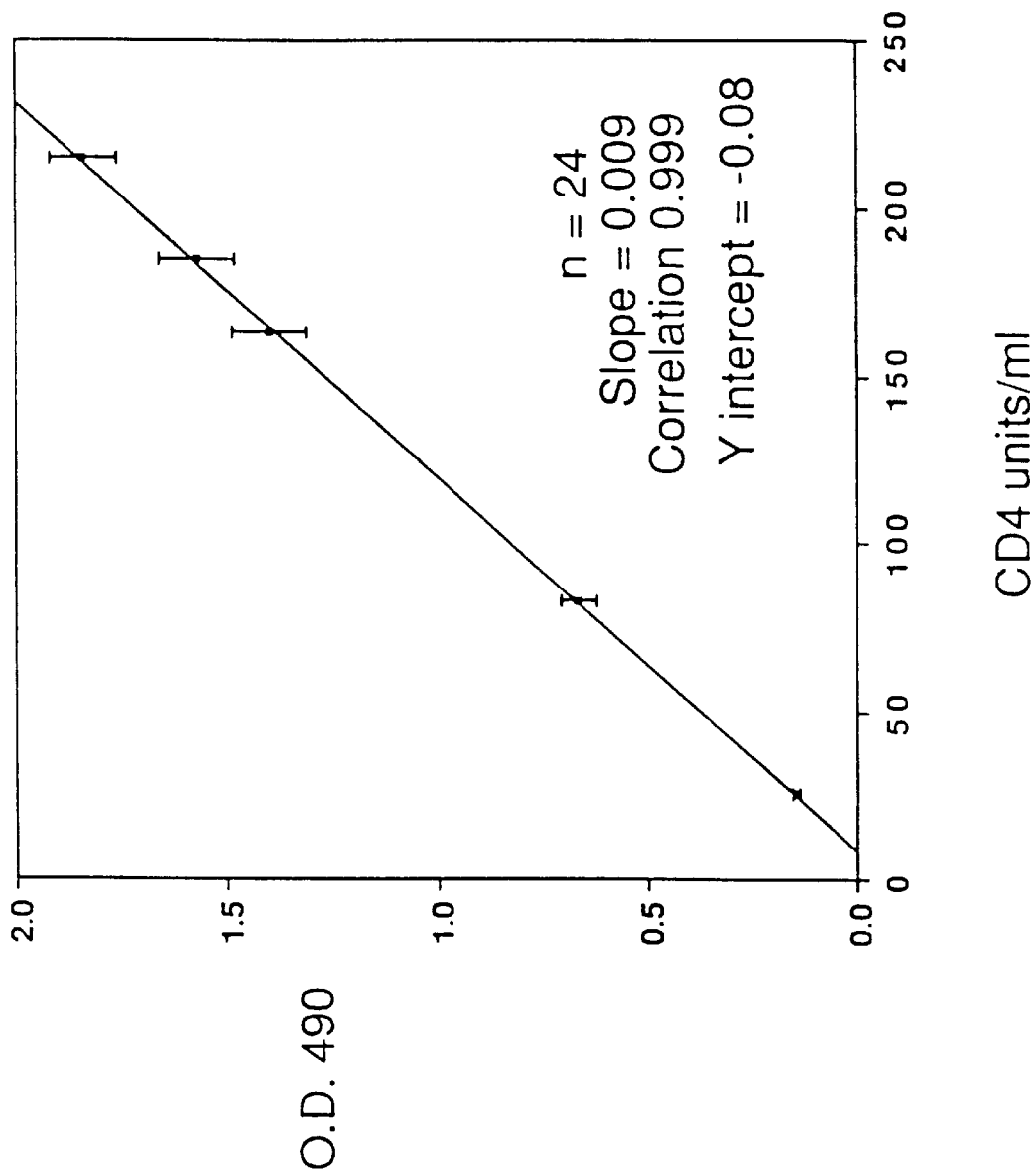

FIG. 5. Total CD4 antigen method standard curve.

Figure 6:
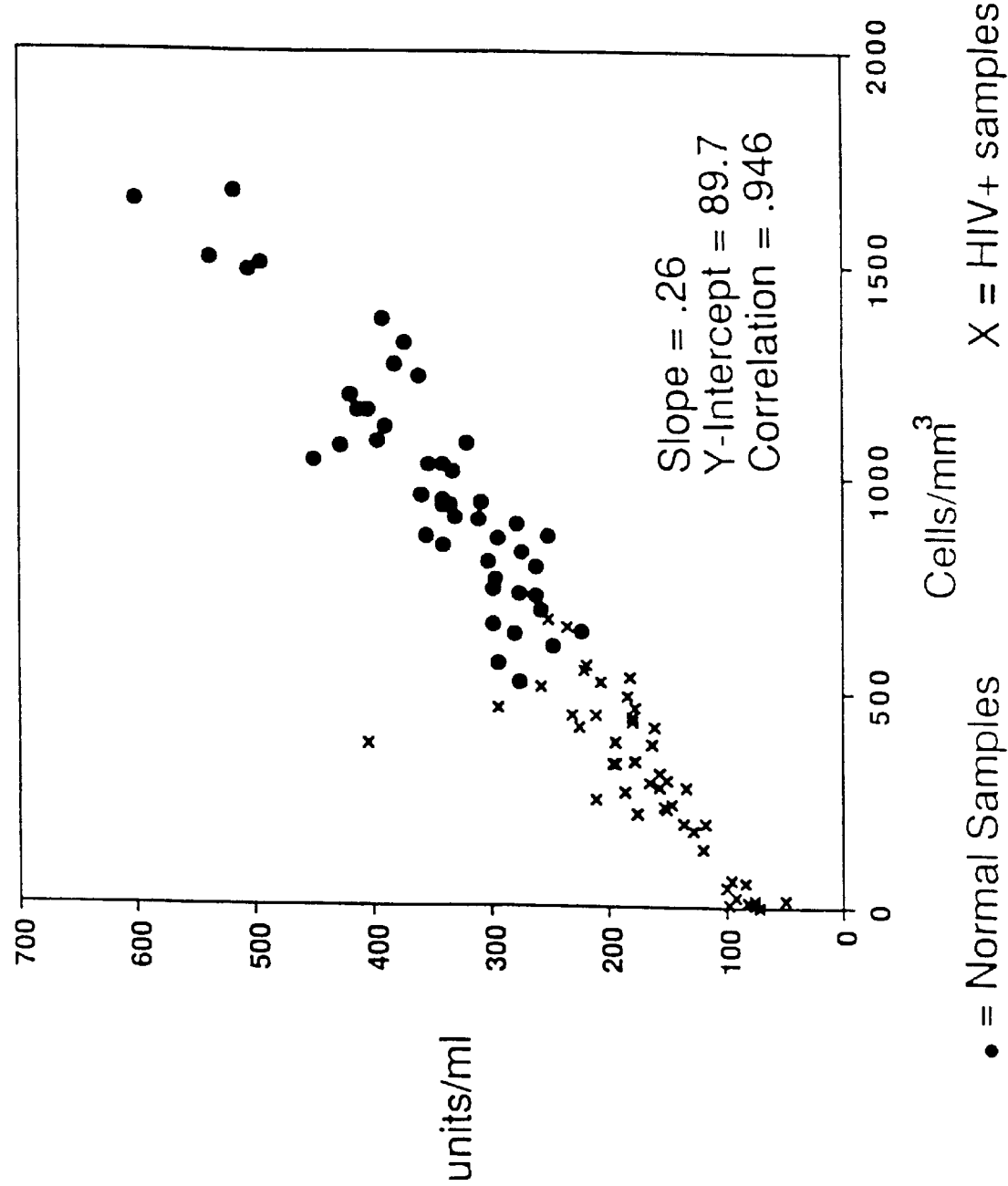

FIG. 6. Comparison of the ability to enumerate CD4 positive cells by the total CD4 antigen method and by flow cytometry in 95 normal and disease samples.

Figure 7:
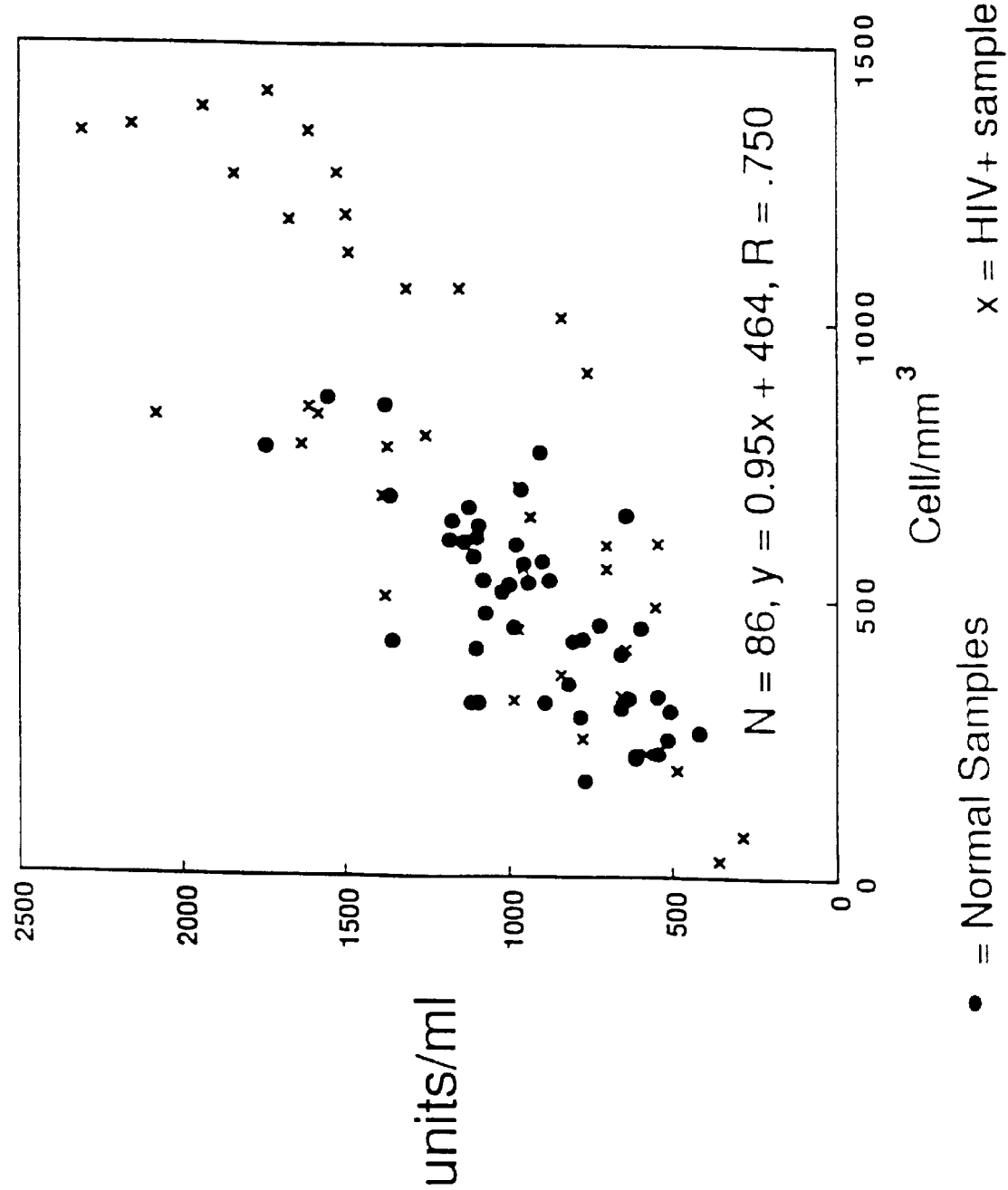

FIG. 7. Comparison of the ability to enumerate CD8 positive cells by the total CD8 antigen method and by flow cytometry in 86 normal and disease samples.

Figure 8:
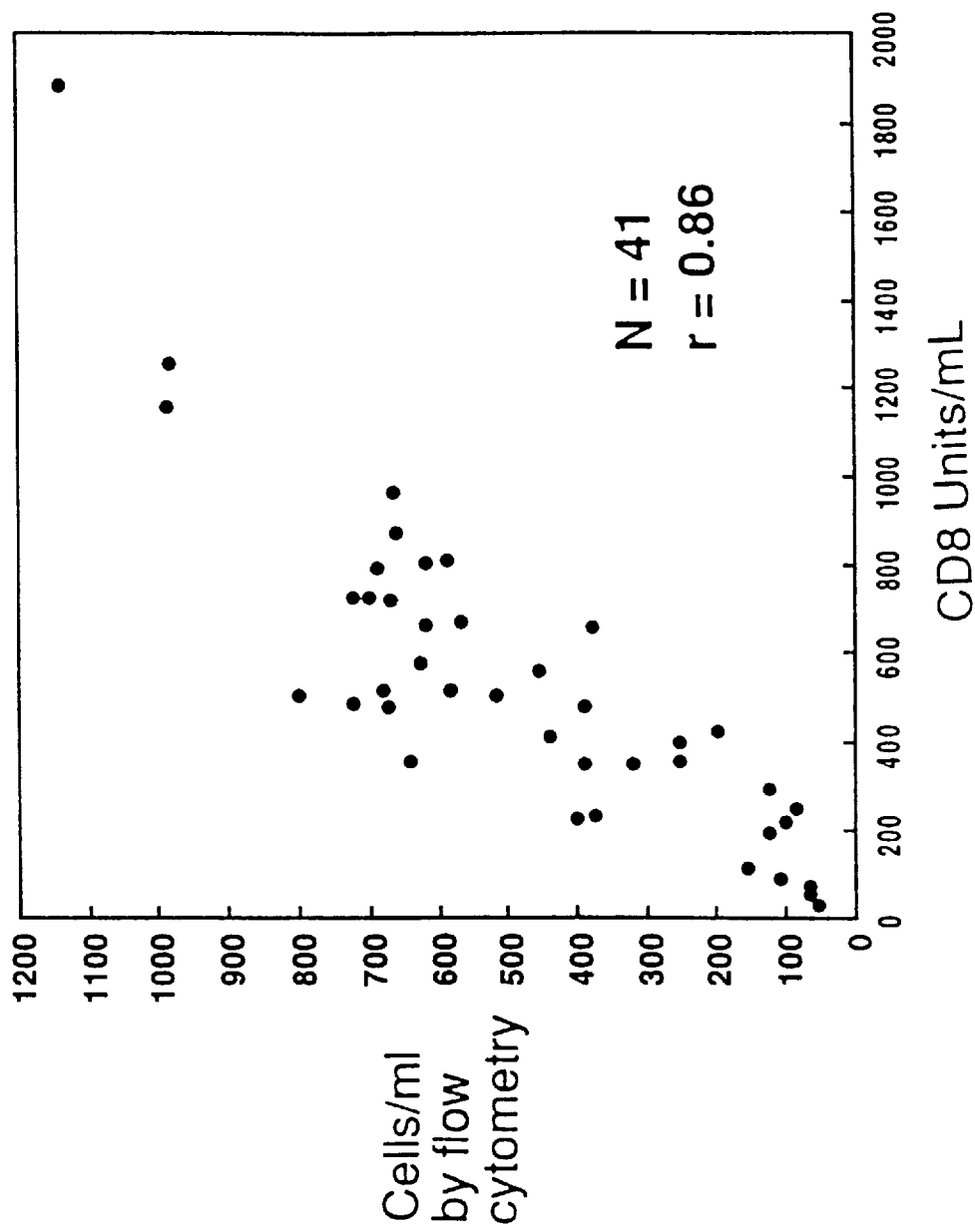

FIG. 8. Cell associated CD8 (total CD8 antigen minus soluble CD8 antigen) in whole blood of 30 normal and 11 cancer patients.

Figure 9:
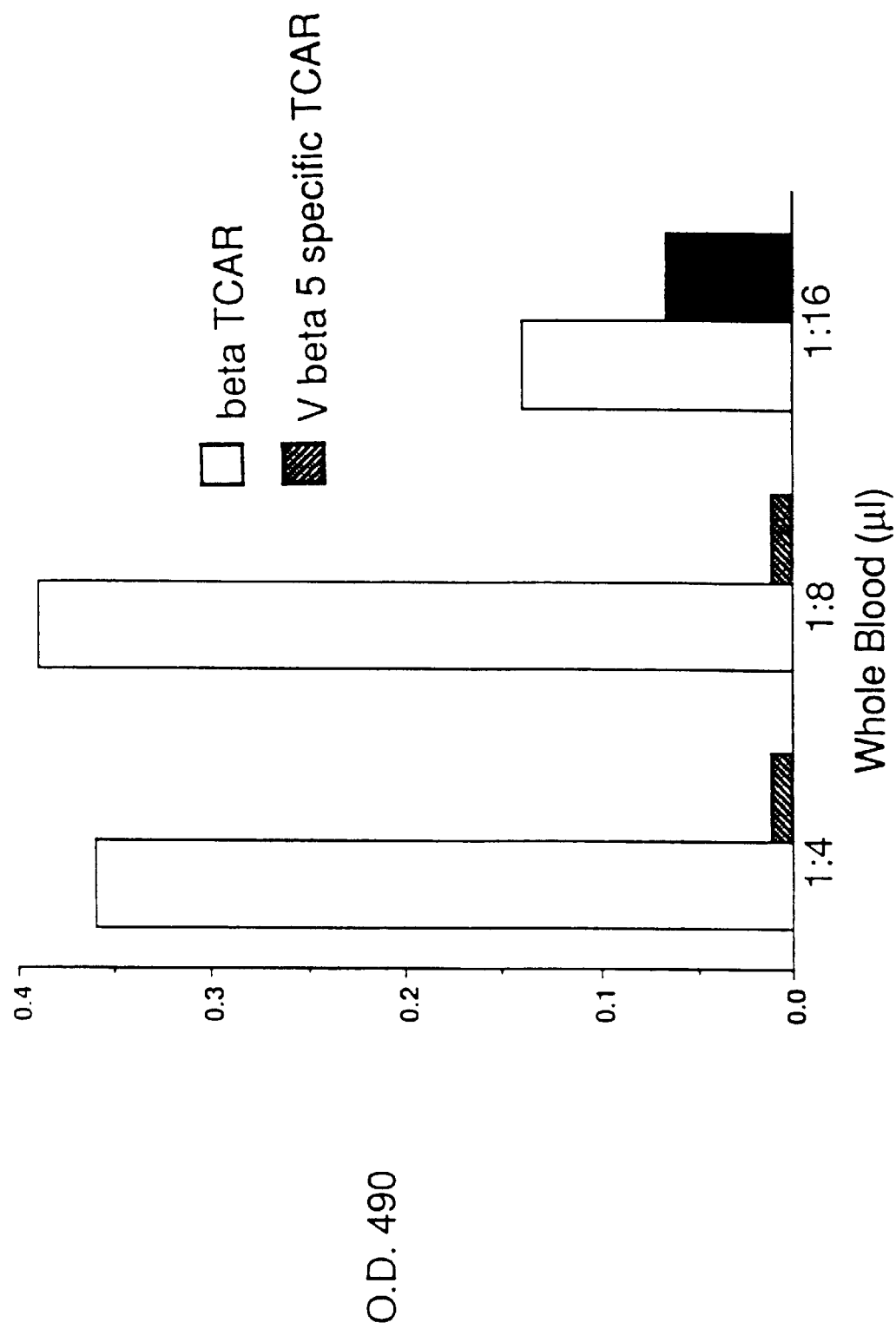

FIG. 9. Total T cell antigen receptor β chain antigen in whole blood of a normal healthy donor.

Figure 10:
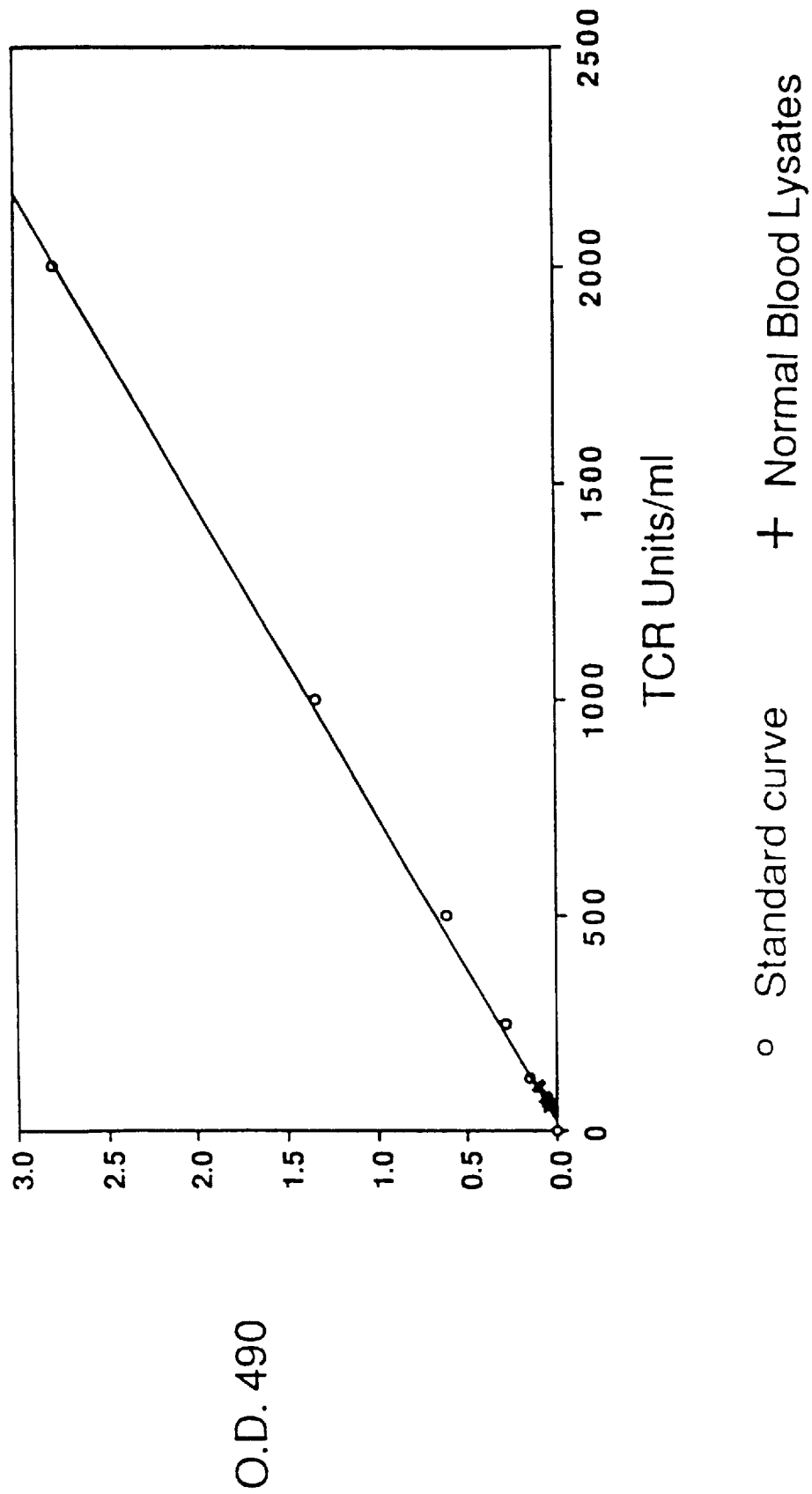

FIG. 10. Total T cell antigen receptor Vδ1 chain antigen and immunoassay standard curve.

5. DETAILED DESCRIPTION OF THE INVENTION

The present invention is directed to the measurement of total leukocyte surface antigens, total T cell differentiation antigens, or related total markers or fragments thereof, and the use of such measurements in the diagnosis and therapy of diseases and disorders.

The measurement of total markers according to the invention is valuable in cell enumeration, cell typing, monitoring the effect of a therapeutic treatment on a subject, detecting and/or diagnosing a disease in a subject, in predicting therapeutic outcome or disease prognosis and in evaluating and monitoring immune status of patients. A plurality of total markers can be measured, such as total CD4 antigen and total CD8 antigen. In a preferred embodiment in relation to AIDS, assays are configured such that total CD4 and total CD8 antigens can be measured simultaneously.

As used herein, the term "total" shall mean the total amount of the marker present in the sample. For example, in a particular sample such as a sample that comprises whole blood, the total marker includes the amount of marker present in the cell membrane, intracytoplasmic and soluble serum compartments. The soluble compartment can include both spontaneously released soluble marker as well as soluble recombinant markers that may have been administered as a therapeutic treatment. In another sample, such as in a sample that comprises cells in tissue culture, the total marker includes the amount of marker present in the membrane, intracytoplasmic and cell culture media compartments of the sample. In yet another embodiment in which the sample comprises a tissue, e.g., a biopsy specimen, the total marker includes the amount of marker present in the membrane, intracytoplasmic and interstitial compartments.

As used herein, the term "compartment" modified by membrane, intracytoplasmic, and soluble elements of a sample refers to the total amount of all membrane, the total amount of intracytoplasmic contents, and the total amount of soluble material included in the sample.

As used herein, the term "leukocyte marker" refers to an antigen or polypeptide found on the cell surface of a leukocyte. Such markers include but are not limited to cell surface antigens, CD (clusters of differentiation) antigens, receptors, or other cell surface polypeptides or proteins. The term leukocyte marker is further intended to include an immunologicaly active fragment, e.g., an epitope, of the foregoing molecules. The leukocyte markers for detection according to the present invention, and the articular cells known to express these markers, are summarized in Table I in Section 2.1, supra. In specific embodiments, the leukocyte marker can be CD4, CD8 or T cell antigen receptor (TCAR).

As used herein, the term "leukocyte" refers to the usual meaning of that terms, i.e., immune associated cells derived from hematopoietic stem cells, such as lymphocytes (B cells and T cells) and myeloid lineage cells (neutrophils, macrophages, eosinophils, megakaryocytes, erythrocytes, mast cells).

As used herein, a "sample" refers to a collection of cells in the milieux in which they were obtained, i.e., a biological fluid, or to membrane and/or intracytoplasmic components of the cells. Total leukocyte antigens may be measured in samples derived from a biological fluid, e.g., whole blood, plasma, serum, blood cells, saliva, urine, synovial fluid, pleural effusions, tumor and tissue infiltrates, amniotic fluid, spinal fluid or cranial fluid. In another embodiment, the biological fluid may be cell culture fluid. The sample can comprise tissue, including interstitial fluid. Preferably when the sample is a tissue sample, the tissue is treated to disrupt the connective tissue matrix, e.g., by trypsin digestion or homogenization. In another embodiment, the sample comprises cells derived from the foregoing sources.

5.1. DETECTION AND MEASUREMENT OF TOTAL LEUKOCYTE MARKER

The total amount of a leukocyte marker exists in three compartments: the membrane, intracytoplasmic and released/soluble compartments ("total leukocyte marker"). The invention includes immunoassays that simultaneously measure the total amount of a leukocyte marker present in all three compartments or in the membrane and/or intracytoplasmis compartment, depending upon how the sample is prepared.

To determine the total amount of a leukocyte marker, an "original" sample, such as whole blood or blood cells, is first treated to solubilize the cellular components (step 1). The preferred method of solubilizing the cells in the sample without interfering with immunospecific binding is to treat the cells with a concentrated non-ionic detergent or detergents to lyse the cells efficiently, thus forming a "detergent-treated" sample. After the cells have been lysed the detergent-treated sample is diluted prior to assay.

Non-ionic detergents for use in present invention include but are not limited to TRITON® X-100 (polyethylene glycol-p-isooctylphenyl ether; octyl-phenoxypolyethoxyethanol), NONIDET® P-40 (polyethylene glycol-p-issoctylphenyl ether; octyl-phenoxypolyethoxyethanol) Tween-20 polyoxyethylenesorbitan, CHAPS (3-[(3-cholamidopropyl)-dimethylammoniol]-1-propane-sulfonate) to mention a few. In a preferred embodiment, cells are solubilized with TRITON® X-100, NONIDET® P-40, Tween-20 and/or CHAPS. In a more preferred embodiment, cells are solubilized with concentrated detergent to give a final detergent concentration of about 2% to about 4% in the detergent-treated sample.

According to the invention, the total volume of non-ionic detergent added to the sample should not dilute out any leukocyte marker in the sample. Preferably, the volume of detergent does not exceed about 25% of the sample volume; more preferably, it does not exceed about 20%. The non-ionic detergent or detergents can be added to the original sample neat, or they can be prepared in a concentrated solution. In addition to the non-ionic detergent or detergents, the concentrated detergent solution can comprise distilled water or buffer. The concentration of non-ionic detergent or detergents in the solution will preferably be 5 times, and more preferably 6 times the final concentration of the non-ionic detergent or detergents after addition to the sample, i.e., in the detergent-treated sample.

In an even more preferred embodiment, more than one non-ionic detergent is used to lyse the cells. For example, a high concentration of Tween-20 and TRITON® X-100, or TRITON® X-100 and NONIDET®-40, or NONIDET® 40 and Tween-20 can be used. The concentration of each detergent ranges from about 1% to about 2% after addition to the sample; the total concentration of detergent in the detergent-treated sample ranges from about 2% to about 4%. More preferably the total detergent concentration ranges from about 2% to about 3%; and even more preferably from about 2% to about 2.5%. In a specific embodiment, the final detergent concentration in the sample is 1.5% TRITON® X-100 and 1% NONIDET®. This is concentration preferred if both CD4 and CD8 are to be assayed.

In another embodiment, the detergent concentration is a concentration that inactivates virus, especially HIV. It is a particular advantage of the invention that the lytic concentration of non-ionic detergent, such as the preferred ranges set forth above, is also a virus-inactivating concentration.

Other methods of solubilizing cells, e.g., repeated freeze-thaw cycles, sonication, hypotony, or the addition of lower concentrations of detergents, are not as effective. Ionic detergents such as SDS are not effective, since SDS interferes with the subsequent antibody-antigen binding.

After solubilization for at least about one minute, preferably for about one to about five minutes, the sample is diluted with buffer (step 2) prior to analysis in an immunoassay. The dilution can be 2-fold; preferably it is 5-fold or greater. The buffer is chosen to be compatable with the immunoassay for detecting the leukocyte antigen. Buffers preferred for various immunoassays are well known in the art. In a specific embodiment, sample buffer is 1% bovine serum albumin, 0.25% NONIDET® P-40 and 0.01%$ thimerosal in phosphate buffered saline (PBS).

The present method is not limited by the amount of sample available. In one embodiment, about 100 $\mu$l of a detergent-treated sample of whole blood may be assayed for total leukocyte antigen. In a more preferred embodiment, about 2.5 to about 25 $\mu$l of a detergent-treated sample of whole blood may be used. Similar amounts of a sample of culture suspension, pleural effusion, or other biological fluid can be used. The actual amount of sample assayed can be varied by adjusting the dilution factor. Determination of specific parameters can be accomplished by a simple dilution series assay, and is well within the level of ordinary skill in the art.

Furthermore, a solubilized sample may be stored frozen so that samples taken at different times may be assayed in a single experiment. In one embodiment, the sample is stored at about –20° C. In a preferred embodiment, the sample is stored at about –70° C.

Any method of detecting and measuring leukocyte antigens may be used in the practice of this invention. Such methods include but are not limited to competitive and non-competitive assay systems using techniques such as radioimmunoassays, ELISA (enzyme linked immunosorbent assay), "sandwich" immunoassays, immunoradiometric assays, fluorescent immunoassays, and protein A immunoassays, to name but a few. U.S. Pat. Nos. 4,845,026, issued Jul. 4, 1989, entitled "Assay Systems for Detecting Cell-Free T Cell Antigen Receptor Related Molecules and Clinical Utilities of the Assays" and U.S. Pat. No. 5,006,459, issued Apr. 9, 1991, entitled "Therapeutic and Diagnostic Methods Using Soluble T Cell Surface Molecules" teach preferred methods of immunoassay. Their teachings are incorporated herein by reference.

In a preferred embodiment, a sandwich enzyme immunoassay can be used. One description of such an embodiment follows: An antibody (capture antibody, Ab1) directed against the leukocyte marker is adsorbed onto a solid substratum. The leukocyte marker present in the sample binds to the antibody, and unreacted sample components are removed by washing. An enzyme-conjugated antibody (detection antibody, Ab2) directed against a second epitope of the leukocyte marker binds to the antigen captured by mab1 and completes the sandwich. After removal of unbound Ab2 by washing, a substrate solution is added to the wells. A colored product is formed in proportion to the amount of antigens present in the sample. The reaction is terminated by addition of stop solution and absorbance is measured with a spectrophotometer. A standard curve can be prepared from known concentrations of the leukocyte marker, from which unknown sample values can be determined.

In a preferred embodiment for the measurement of total CD8 antigen levels, anti-CD8 mAbs 4C9 and 5F4 can be used as the capture and detection antibodies, respectively, in a sandwich enzyme immunoassay; in a more preferred embodiment, a CELLFREE® CD8 assay (T Cell Sciences, Inc., Cambridge, Mass.) can be used (described in U.S. Pat. No. 5,006,459; see Section 8, infra). In a preferred embodiment for the measurement of total CD4 antigen levels, anti-CD4 mAbs 8F4 and R2B7 can be used as the capture and detection reagents, respectively, in a sandwich enzyme immunoassay; in a more preferred embodiment, a CELL-FREE® CD4 assay (T Cell Sciences, Inc., Cambridge, Mass.) can be used (described in International Patent Publication WO 90/04180; see Sections 6 and 7, infra). In a preferred embodiment for the measurement of total Vδ1 antigen levels, anti-TCRδ mAbs TCRδ1 and δTCS1 can be used in a sandwich enzyme immunoassay (see Section 9, infra). In a preferred embodiment for the measurement of total β TCR antigen levels, anti-βTCR mAbs βF1 and W4 can be used in a sandwich enzyme immunoassay (see Section 10, infra). The foregoing antibodies have been deposited with the ATCC, as described in Section 10, infra.

Various procedures known in the art may be used for the production of antibodies to leukocyte marker. Such antibodies include but are not limited to polyclonal, monoclonal, chimeric, single chain, Fab fragments and an Fab expression library. For the production of antibodies, various host animals, including but not limited to rabbits, mice, rats, etc., may be immunized by injection with a leukocyte marker. In one embodiment, leukocyte marker may be conjugated to an immunogenic carrier. In another embodiment, leukocyte marker epitope, e.g., a hapten, is conjugated to a carrier. As used herein, an "epitope" is a fragment of an antigen capable of specific immunoactivity, e.g., antibody binding. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies to leukocyte marker may be prepared by using any technique which provides for the production of antibody molecules by continuous cell lines in culture. These include but are not limited to the hybridoma technique originally described by Kohler and Milstein, (1975, *Nature* 256: 495–497), the more recent human B-cell hybridoma technique (Kosbor et al., 1983, *Immunoloqy Today* 4: 72) and the EBV-hybridoma technique (Cole et al., 1985, *Monoclonal Antibodies and Cancer Therapy*, Alan R. Liss, Inc., pp. 77–96). In an additional embodiment of the invention, monoclonal antibodies specific for leukocyte marker may be produced in germ-free animals utilizing recent technology (PCT/US90/02545). According to the invention, human antibodies may be used and can be obtained by using human hybridomas (Cote et al., 1983, *Proc. Nat'l. Acad. Sci., U.S.A.* 80: 2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, *Proc. Nat'l. Acad. Sci. U.S.A.* 81: 6851–6855; Neuberger et al., 1984, *Nature* 312: 604–608; Takeda et al., 1985, *Nature* 314: 452–454) by splicing the genes from a mouse antibody molecule specific for leukocyte marker together with genes from a human antibody molecule of appropriate biological activity can be used; such antibodies are within the scope of this invention.

According to the invention, techniques described for the production of single chain antibodies (U.S. Pat. No. 4,946,778) can be adapted to produce a leukocyte marker-specific single chain antibody. An additional embodiment of the invention utilizes the techniques described for the construction of Fab expression libraries (Huse et al., 1989, *Science* 246: 1275–1281) to allow rapid and easy identification of monoclonal Fab fragments with the desired specificity for leukocyte marker.

Antibody fragments which contain sites specific for leukocyte marker may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments.

The above-described method can also be used to assay any total leukocyte surface marker, e.g., the markers described in Sections 2.1 supra. For example, and not by way of limitation, total CD4, total CD8, or total TCR may be measured in the practice of this invention. In another embodiment, a plurality of two or more total leukocyte surface molecules or markers can be measured. In yet a further embodiments, the relative amount of one marker can be compared to another.

5.2. ENUMERATION OF LEUKOCYTES POSITIVE FOR A MARKER

The measurement of a total leukocyte marker according to the invention provides a method to enumerate the number of leukocytes that are positive for the leukocyte marker in a sample. In another embodiment, the activity of a leukocyte marker in an assay can be compared to the activity of a standard that comprises a known number of cells positive for the leukocyte marker.

This aspect of the invention is based on the discovery that the total leukocyte marker level in a sample, which is proportioned to the activity of the leukocyte mark in an assay for the leukocyte marker, correlates directly with the number of cells positive for that marker. As shown in an Example, infra (Section 7), the correlation between the number of CD4+ cells determined according to the present invention and the number of cells determined by fluorescence-activated cell sorting (FACS) has a correlation coeffecient of 0.946, which indicates that enumeration of a leukocyte marker-positive cell by the total leukocyte marker method of the invention can be as reliable as enumeration by flow cytometry. Furthermore, as pointed out in the Summary of the Invention, supra, the present methods do not require complicated sample preparation, careful storage conditions, or expensive analytical equipment.

In another embodiment, the amount of leukocyte marker in the membrane and/or intracytoplasmic compartments of a sample, i.e., not including soluble leukocyte marker, correlates with the number of cells in the sample. As shown in an Example, Section 8 infra, the correlation between the number of cells positive for a leukocyte marker and the amount of leukocyte marker in the membrane and intracytoplasmic compartments is good.

According to the present invention, the number of cells positive for a leukocyte marker in a sample can be determined by (1) determining the total amount of leukocyte marker in a sample, and (2) calculating the total number of cells positive for the leukocyte marker from the total amount of leukocyte marker. In one embodiment, the calculation can be made by extrapolating from a standard curve of total leukocyte marker versus total number of cells positive for the leukocyte marker. In another embodiment, a formula can be derived from a standard curve, and the total amount of leukocyte marker plugged into the formula. In yet another embodiment, only the activity of the assay for a total leukocyte marker is used to calculate the total number of cells positive for the marker. In this embodiment, the total amount of leukocyte marker is reflected in the relative activity in the detection assay. The method of calculating a total number of cells, e.g., extrapolation or a formula, remains the same.

The present invention provides simple, straightforward methods to calculate a standard. In one embodiment, the total amount of leukocyte marker relates to the total number of cells positive for the marker. In a more preferred embodiment, a linear regression analysis of the total leukocyte marker to total cell number positive for the marker is performed. The linear regression analysis can yield a straight line curve, an estimate of error, and a formula for calculating total cell number from total leukocyte marker amount.

In another embodiment, the activity of the leukocyte marker in the detergent-treated sample can be detected by immunological detection means and compared with an assay of a known amount of leukocyte marker in a standard sample, and the number of cells positive for the leukocyte marker determined from the comparison. In a more preferred embodiment, the activity in an assay of the leukocyte marker in the detergent-treated sample can be compared with the activity in an assay of the leukocyte marker in a standard containing a known number of cells positive for the marker, and the number of cells positive for the leukocyte marker in the sample determined from the comparison.

In another embodiment, the correlation of total leukocyte marker with cell number positive for that marker can be corrected for an excess amount of leukocyte marker in the soluble or total compartment. The amount of soluble leukocyte marker can be assayed by the same immunological detection means, e.g., using the same immunoassay. The amount of soluble marker can be subtracted from the amount of total marker. The corrected cell-associated leukocyte marker value can correlate more accurately with the cell count. In a specific embodiment, the total number of CD8+ cells correlates with the total amount of CD8 minus soluble CD8 (see Section 8, infra).

In preparing a standard, total cell number can be independently determined by any means known in the art, e.g., FACS, immunofluorescence microscopy, and complement lysis assays, to mention a few. In a preferred embodiment, the independent total cell number is obtained by FACS.

A total CD4 assay may be used to estimate the member of CD4+ T cells in a patient sample. The estimate of the number of CD4+ T cells in a sample can be used for diagnosis or monitoring of a therapeutic treatment, e.g., for AIDS patients.

In a preferred embodiment, CD8+ cells can be enumerated by measuring the total amount of CD8 antigen in the sample and subtracting the amount of soluble CD8 antigen in the same sample. Such an analysis yields information on both the immune system activation and the CD8+ cell count.

In yet a further embodiment the total number of T cells positive for $\alpha\beta$ or $\gamma\delta$ TCAR can be determined. Similarly, the total number of T cells positive for subsets of $V\alpha$, $V\beta$, $V\gamma$ or $V\delta$ can be determined. Thus, whole blood samples can now be analyzed quickly, safely and reliably for the number of specific subsets of T cells.

5.3. KITS

The reagents necessary for the practice of the present invention can be conveniently provided in a kit. The essential elements of a kit of the invention are a concentrated non-ionic detergent solution and a means for immunologically detecting the presence of an antigen.

The kit can comprise any immunological detection means known in the art, e.g., those discussed in Section 5.1., supra. Preferably the immunological detection means are a first capture antibody specific for a leukocyte marker, and a second detectable antibody specific for the leukocyte marker. The first antibody can be provided on a solid support, such as a glass or plastic bead, membrane, a plastic stick, a microwell, a glass or plastic test tube, or other solid supports known in the art for immunoassays. Alternatively, the first antibody can be provided for later immobilization. The first and second antibodies can be provided as a lyophilized preparation for reconstitution, or as a concentrated solution. The second antibody can be detectable by labeling means. In a preferred embodiment, the labeling means is an enzyme.

The detergent solution is provided in a container having sufficient volume to hold the amount of solution necessary for the number of assays contemplated by the kit. Preferably the detergent solution comprises two or more non-ionic detergents. In a preferred embodiment, the detergent solution comprises 9% TRITON® x-100 and 6% NONIDET® P-40 in distilled water. That particular detergent concentration is optimum with respect to an assay for both CD4 and CD8.

Preferably the kit comprises a leukocyte marker standard, either in solution or lyophilized for reconstitution. More preferably, the kit comprises a standard comprising a known number of cells positive for the leukocyte marker of interest. Thus, the activity in an assay for the leukocyte marker in an unknown sample can be directly compared with a known sample, and the number of cells in the unknown sample that are positive for the leukocyte marker enumerated thereby.

The kit can further comprise a reagent reactive with label, when the second antibody is detectable by attachment of a label to the antibody. For example, when the label is an enzyme, the kit can provide the enzyme substrate. The kit can also provide a dilution buffer, in final concentration, high concentration for dilution, or dry for reconstitution.

In yet a further embodiment, a kit provides immunological detection means for more than one leukocyte antigen. In a preferred embodiment, the kit comprises immunological detection means for both CD4 and CD8.

5.4. METHODS OF DIAGNOSIS AND MONITORING OF A DISEASE

5.4.1. METHODS OF DIAGNOSIS

In another embodiment of the present invention, measurement of a total leukocyte marker can be used to detect, diagnose or stage a disease or disorder in a subject. The measured amount of the total leukocyte marker is compared to a baseline level, i.e., the amount of total leukocyte marker in normal individuals. This baseline level can be the amount which is established to be normally present in the body fluid of subjects prior to the onset of disease or the amount present during remission of disease.

Disease or disorders which may be detected, diagnosed or staged in a subject according to the present invention include but are not limited to those listed in Table III.

TABLE III

DISEASES AND DISORDERS WHICH MAY BE DETECTED AND/OR DIAGNOSED AND/OR MONITORED IN A SUBJECT ACCORDING TO THE PRESENT INVENTION

| | |
|---|---|
| I. | Infectious Diseases Induced by virus |
| | Herpesvirus |
| | Cytomegalovirus |
| | Etpstein-Barr Virus |
| | HTLV-I |
| | HTLV-III/LAV/HIV (AIDS) |
| II. | Cancer |
| | B or T cell leukemia |
| | HTLV-I- associated adult T cell leukemia |
| | B or T cell lymphoma |
| | Burkitt's lymphoma |
| | Hairy cell leukemia |
| | Sezary syndrome |
| | Hodgkin's disease |
| | Chronic lymphocytic leukemia |
| | Non-Hodgkin's lymphoma |
| | B-cell acute lymphoblastic leukemia |
| | Solid tumors |

TABLE III-continued

DISEASES AND DISORDERS WHICH MAY BE DETECTED AND/OR DIAGNOSED AND/OR MONITORED IN A SUBJECT ACCORDING TO THE PRESENT INVENTION

| | |
|---|---|
| III. | Autoimmune Diseases |
| | Rheumatoid arthritis |
| | Diabetes |
| | Multiple sclerosis |
| | Systemic lupus erythematosis |
| IV. | Organ Allograft Rejection |

The methods for detecting diseases or disorders based on the number of cells in a sample from the patient that are positive for a leukocyte marker are discussed in Section 2.3 supra and in the references cited therein. Those methods can be practiced by the present methods of the invention more cheaply and easily than heretofore thought possible.

In one embodiment, the amount of total CD4 antigen can be used to enumerate CD4 positive cells which in turn can be used to diagnose AIDS. In the past, the diagnosis of AIDS was determined when a patient who was HIV-positive demonstrated CD4 positive cell counts of <500 cells/mm$^3$ in the presence of one or more opportunistic infections. This definition of AIDS is expected to change to HIV-positive in the presence of <200 cells/mm3 whether or not opportunistic infections are present (see Section 2.3., supra).

Responses to viral infections can also be monitored by measuring total CD8 levels in a patient. For example, patients infected with herpes virus or an AIDS virus can present modified levels of total CD8. In other embodiments, total levels can be measured in transplant patients, and used as a diagnostic indication of allograft rejection. Detection of increased levels of total CD8 can be associated with rheumatoid arthritis and infectious diseases such as EBV-induced mononucleosis. Detection of elevated levels of a CD8 antigen can indicate the involvement of significant numbers of suppressor/cytotoxic T cells with a specific pathological event, distinct from immune activation.

In yet another embodiment, the measurement of total CD4 in a cell culture can be relied on as an indication of the CD4$^+$ phenotype of the lymphocytes present. For example, CD4$^+$ leukemias or lymphomas can be classified using total CD4 antigen measurements. In a further embodiment, the measurement of total CD4 antigen can be used to detect CD4$^+$ cells and to enumerate them. Similar embodiments of the invention include the measurement of total CD8 antigen to classify CD8$^+$ leukemias or lymphomas, to detect CD8$^+$ cells and to enumerate them.

5.4.2. METHODS OF MONITORING

The present invention provides a method for monitoring the effect of a therapeutic treatment on a subject who has undergone the therapeutic treatment. This method comprises measuring at suitable time intervals the amount of a total leukocyte marker. Any change or absence of change in the amount of the total leukocyte marker can be identified and correlated with the effect of the treatment on the subject.

In one embodiment, total CD4 can be measured (and CD4$^+$ cells enumerated) and used in the prediction of therapeutic outcome of AIDS patients following administration of therapeutic compounds such as AZT, interferon or CD4.

In another embodiment, total CD8 antigen can be measured and correlated with disease progression or treatment outcome.

Measurement of total T cell antigen receptor can be especially useful in monitoring the effectiveness of treatment with agents such as T cell receptor specific antibodies. In specific embodiments, the total TCR antigen in a specific subset of T cells expressing specific variable regions can be measured and correlated with treatment outcome.

The therapeutic treatments which may be evaluated according to the present invention include but are not limited to radiotherapy, drug administration, vaccine administration, immunosuppressive or immunoenhansive regimens, etc. The immunosuppressant regimens include, but are not limited to administration of drugs such as Cyclosporin A, chlorambucil, cyclophosphamide, or azathioprine, and anti-T cell antibody such as anti-T3 monoclonal antibody, anti-T cell antigen receptor antibody, and anti-thymocyte globulin, etc. The immunoenhansive regimens include, but are not limited to administration of interleukin-1, interleukin-2, interleukin-4 and other T cell growth actors.

5.4.3. METHODS OF DIAGNOSIS OR MONITORING OF THERAPY BASED ON DETECTION OF A PLURALITY OF LEUKOCYTE MARKERS

The present invention also provides for the detecting or diagnosis of disease, or the monitoring of treatment by measuring a plurality (at least two) of total leukocyte markers. For example, a plurality of T cell markers either in total form, for example but not limited to CD4 and CD8, and TCAR to mention but a few, can be measured to diagnose, detect, or monitor treatment of diseases or disorders. Such diseases or disorders include those indicated in Table III. Total marker levels can represent a measure of immune system function, paralleling disease course or treatment efficacy. In a preferred embodiment, the prognostic indicator is the observed change over time in different marker levels relative to one another, rather than the absolute levels of the markers present at any one time. Since CD4, CDs and TCAR are indicators of the immune system function, they should provide a much improved measure of the relative health of the immune system during various stages of disease or disorders.

In a particular embodiment, diseases and disorders caused by HIV (the causative agent of AIDS) infection may be monitored by measurements of a plurality of leukocyte surface markers. AIDS therapies include-the treatment of AIDS patients with drugs such as AZT (azido-deoxythymidine), γ or β interferons, and with soluble CD4, or its fragments and derivatives. In another embodiment, the efficacy of potential AIDS vaccines, such as gp120 peptides can be tested by monitoring a plurality of markers. Practitioners in AIDS therapy very much need a procedure that can be used to monitor the efficacy of these treatments or vaccines. To date, the levels of the HIV antigen p24 have not proved sensitive enough. Total CD4 relative to total CD8 can be detected in HIV-infected patients with different manifestations of disease, providing a sensitive immunoassay to monitor AIDS therapies and vaccines. The measurement of total CD4 and total CD8 is an inexpensive and easy immunoassay format and is a valuable clinical tool for predicting disease prognosis and treatment outcome in AIDS patients. Detection of total CD4 and CD8 according to the method of the invention antigen provides a particularly useful way to follow HIV infection and AIDS therapy since the relative level of CD4 positive T cells decrease dramatically relative to the total number of CD8 positive cells in the progress of AIDS etiology.

In a preferred aspect, the approach that can be taken is to determine the levels of total CD4 and total CD8 levels in longitudinal time studies and to compare these values with a baseline level. The baseline level can be either the level of the marker present in normal, disease-free individuals or the level present in a patient prior to treatment, during remission of disease, or during periods of stability. These levels can then be correlated with the disease course or treatment outcome.

The present invention also provides for the detection or diagnosis of disease or the monitoring of treatment by measuring the amounts of total leukocyte marker and of soluble leukocyte marker in a sample and comparing the two measurements. The change in the levels of the leukocyte markers relative to one another can be an improved prognostic indicator. In one embodiment, the level of soluble CD8 (a measure of immune system activation, see International Patent Publications WO 87/05912 published Oct. 8, 1987 and WO 90/04180 published Apr. 19, 1990) is compared with the level of CD8 antigen obtained by subtracting the amount of soluble CD8 antigen from the amount of total CD8 antigen (e.g., the difference yields cell membrane bound plus cytoplasmic CD8, which is equivalent to cell-associated total CD8). Such a comparison gives information on the relative level of immune system activation and on changes in the number of cells in the CD-positive cell subset, both useful in the monitoring of disease progression or treatment. In a preferred embodiment, both the soluble and total CD8 antigen levels can be determined using one immunoassay configuaration, but with different sample treatment before assay.

The instant invention will be further clarified by the following Examples, which are provided as purely exemplary of the invention and are not intended as limiting of the invention.

6. EXAMPLE: A TOTAL CD4 ANTIGEN ASSAY

The present example demonstrates the development of an assay that correlates total CD4 values with the number of CO4$^+$ T cells in a sample.

6.1. MATERIALS AND METHODS

6.1.1. SAMPLE PREPARATION

Samples. Patient samples included 26 sero-positive HIV-infected individuals and 13 healthy adult volunteers. Blood was obtained by venipuncture into a blood collection tube.

Sample Treatment. Prior to assay, whole blood samples were treated as follows.
Step 1:
100 µl of anticoagulated blood was removed from the blood collection tube and mixed with 20 µl of concentrated 6x detergent (6% TRITON® X-100, 6% NONIDET® P-40 in distilled water) in a 12×75 mm glass tube. This mixture was then incubated for one minute at room temperature. After one minute the treated sample was either used in a CD4 immunoassay or stored at −70° C. until assayed. Samples stored at −70° C. were allowed to thaw at room temperature before use.
Step 2:
Prior to assaying the treated samples in a CD4 immunoassay, the samples were diluted as indicated in the results section with sample buffer (1% bovine serum albumin, phosphate buffered saline, 0.25% NONIDET® P-40 and 0.01% thimerosal) to dilute the concentration of detergent. Total sample volumes added to the immunoassay were maintained at 50 µl.

6.1.2. CD4 IMMUNOASSAY

Total CD4 antigen was measured in a CD4 specific immunoassay (see International patent publication WO 87/05912 published Oct. 8, 1987) involving a one-step, three hour format using microtiter plates that had been precoated with capture antibody overnight. Briefly, each well of a 96 well microtiter well plate was coated with 100 µl of murine anti-CD4 coating antibody in phosphate-buffered saline (PBS) overnight at 4° C. Any remaining protein-binding sites were blocked with 300 µl per well of blocking buffer (0.5% casein, 0.008% NONIDET® P-40, 0.005% EDTA in PBS) for 2 hours at 37° C. The wells were washed three times with 350 µl per well of wash buffer (PBS, ph 7.4, with 0.05% Tween 20). After aspirating the final wash buffer from the wells, 50 µl of horseradish peroxidase (HRP) conjugated murine monoclonal anti-human CD4 antibody (in PBS with 15% FCS and 0.15% NONIDET® P-40) and 50 µl of sample or standard were added to each well of the microtiter plate in duplicate. The combined volume of sample and HRP conjugated antibody was 100 µl. Samples and antibodies were incubated for 3 hours at room temperature. After washing the plate as described above, 100 µl of OPD substrate (OPD tablets, BioDesign Intl, Catalogue # A45104T, dissolve 1 tablet in 4 ml citrate buffer-peroxide, BioDesign Intl, Kennebunkport, Me., Catalog number A45105B) was added to all the wells and incubated for 30 minutes at room temperature. At the end of this last incubation, 50 µl of 2N $H_2SO_4$ was added to each well to stop the reaction and absorbance of each well was read at 490 nm. Results were plotted as values obtained for each sample at O.D. 490 against total CD4$^+$ cells/mm$^3$ or sample volume. Correlation coefficients were calculated using linear regression analysis.

Whole blood samples from normal and HIV-infected patients were assayed for absolute CD4$^+$ T-cells/mm$^3$ using the formula:

$$\text{Abs. CD4}^+\text{T cells/mm}^3 = \text{WBC} \times \% \text{ Lymphocyte} \times \% \text{ CD4}^+\text{T cells.}$$

WBC (White blood cell count) was determined using a hemacytometer. % Lymphocyte was determined by a differential-count, and %CD4$^+$ T cells were determined using the Ortho cytoflurograph II and Leu-3a (anti-CD4) fluorescein-conjugated antibody (Becton Dickinson, Mountain View, Calif.)

6.2. EXPERIMENTAL RESULTS

Experiment 1: Measurement of total CD4 antigen in whole blood. This study was conducted to determine whether detergent treatment of whole blood would yield reliable measurements of total CD4 antigen in a CD4 immunoassay. Samples of whole blood were treated with a 6x detergent solution using a ratio of 20 µl detergent to 100 µl anticoagulated whole blood. Serial dilutions were made of these samples to produce a series of samples containing decreasing amounts of total CD4 antigen. These samples were then analyzed in the CD4 assay to determine which dilutions produced values that were linear with sample dilution. As the assay configuration became saturated with excess CD4, the optical density values representing total CD4 values became nonlinear.

The results of this experiment can be seen in FIG. 1. Total CD4 preparations made from three healthy volunteers were treated with concentrated non-ionic detergent, and diluted in serial 1:2 increments (from ½ to ¹⁄₃₂). Sample volumes were maintained at 50 µl by dilution into sample buffer. Linear regression analysis demonstrated that samples containing less than 20 µl and preferably 5–10 µl of detergent treated whole blood were optimal for total CD4 measurement as they fell within the linear range. Samples containing greater than 20 μl of whole blood saturated the assay and total CD4 could not be accurately determined.

Experiment 2: Specificity of the total CD4 antigen measurement. The ability of an anti-CD4 antibody to block the total CD4 signal detected in whole blood samples of three normal controls is presented in Table IV. The assay was run as described above, except that before adding the HRP-conjugated murine anti-CD4 monoclonal antibody to the wells, 5 μl of the unconjugated murine anti-CD4 monoclonal antibody used in the coating procedure was added to the wells, followed by the HRP-conjugated antibody. Samples were diluted with sample diluent to a final volume of 50 μl. The unconjugated antibody was able to block total CD4 detection by 50%, 51% and 51% in samples #1, 2, and 3, respectively, at the level of competing antibody used. This demonstrates the specificity of the assay to detect total CD4. Other proteins released during detergent lysis of the whole blood samples (such as hemoglobin) did not interfere with the assay.

TABLE IV

SPECIFICITY OF TOTAL CD4 DETECTION IN DETERGENT TREATED WHOLE BLOOD
O.D. 495

| sample # | 10 μl* | 10 μl + anti-CD4** | % inhibition |
|---|---|---|---|
| 1 | 0.433 | 0.216 | 50% |
| 2 | 0.928 | 0.472 | 51% |
| 3 | 0.833 | 0.422 | 51% |

*10 μl of detergent treated whole blood prepared from normal uncoagulated whole blood
**5 μl of the anti-CD4 coating antibody from the CD4 assay was also added to compete for binding.

Experiment 3: Enumeration of cell number using total CD4 values. This study was done to determine whether the measurement of total CD4 levels in treated whole blood samples would correlate with absolute CD4 positive cell numbers. Data in FIG. 2 demonstrate a statistically significant correlation between total CD4 measured in whole blood samples and the total number of $CD4^+$ cells/mm$^3$ of blood (r=0.904). Samples measured in this assay contained 2.5 μl of detergent treated whole blood diluted to a final volume of 50 μl from a total of five normal controls. The normal range of $CD4^+$ cells/mm$^3$ is 800–1000 cells/mm$^3$. The normal values in this assay appear lower than usual due to the fact that the WBC count used to determine the number of CD4 cells/mm$^3$ was performed on the uncoagulated blood samples three days after the CD4 assay was run. The relationship between total CD4 detected in the assay and the total $CD4^+$ cells/mm$^3$ for each individual was determined by linear regression analysis and a statistically significant r value of 0.904 was obtained. This indicates that the measurement of total CD4 antigen can be used to directly enumerate CD4 positive cells.

Experiment 4: Enumeration of $CD4^+$ cells in HIV-infected and normal individuals using measurements of total CD4 antigen. After the properties of the total CD4 method were established using healthy donors, further study was conducted to establish a relationship between the total CD4 as measured in the ELISA to the total number of $CD4^+$ T cells in HIV infected individuals.

The total CD4 antigen values of HIV-infected individuals and normals were determined using the total CD4 method on two separate occasions. The result of these experiments are presented in FIGS. 3 and 4. Ten μl of whole blood samples diluted to a total sample volume of 50 μl from either the disease group or control group were used to determine the total CD4 antigen values. The total $CD4^+$ cells/mm$^3$ cells was determined on fresh uncoagulated blood samples on the day of the CD4 assay.

Both FIGS. 3 and 4 demonstrate a statistically significant correlation between total CD4 antigen measured in the assay and the total $CD4^+$ cells/mm$^3$ for both the HIV-infected group (single squares) and the control group (double squares) (r=0.860 and 0.867 for FIGS. 3 and 4, respectively). Thus, the measurement of total CD4 antigens from detergent treated whole blood accurately reflects the absolute number of $CD4^+$ T-cells in whole blood for both normal and HIV infected individuals.

6.3. DISCUSSION

As described herein, we have developed a method that measures the level of total CD4 antigen in a patient sample. Whole blood samples were detergent treated and assayed using a CD4 immunoassay in a one-step, three hour format. It was demonstrated that total CD4 antigen could be detected in whole blood samples of normal individuals by a simple detergent lysis step and CD4 immunoassay. Optimal detection could be measured using 10 μl or less of detergent treated whole blood samples. Accurate and reproducible measurements can be detained from 2.5 μl to 5 μl of whole blood. The detection of total CD4 antigen was specific as a murine anti-CD4 monoclonal antibody was capable of blocking the total CD4 antigen signal when added to the assay format. The release of other proteins during detergent treatment of whole blood did not interfere with the specificity of the assay. It was further demonstrated that the total CD4 antigen values obtained in the ELISA correlated with the total $CD4^+$ T cells/mm$^3$ in the whole blood of normal donors (r=0.9).

A comparison between the total CD4 antigen obtained in the CD4 ELISA and the total number of $CD4^+$ T Cells/mm$^3$ of whole blood yielded a statistically significant correlation in both HIV-infected individuals and normals. This comparison was determined on two separate occasions using two different groups of HIV-infected individuals and normals. Both comparisons yielded statistically significant correlations between total CD4 antigen values and total $CD4^+$ T cells/mm$^3$ (r=0.86 and 0.87). Since the measurement of total CD4 antigen accurately reflects the number of CD4 positive cells, the total CD4 method can be used to enumerate CD4 positive cells and to determine the numbers of CD4 positive cells in disease diagnosis or monitoring of treatment, etc.

7. EXAMPLE: ENUMERATION OF CD4 POSITIVE LYMPHOCYTES IN PERIPHERAL BLOOD BY THE TOTAL CD4 METHOD

This Example outlines further development and characterization of the total CD4 method for enumeration of CD4 positive cells. The method consists of 3 steps: treatment of samples with concentrated detergent, dilution of the concentrated detergent lysate and CD4 immunoassay.

7.1. MATERIALS AND METHODS

Samples: Ninety-five samples of whole blood were collected in EDTA containing vacutainer tubes and mixed thoroughly. Samples were analyzed for white blood cell count and differential and $CD4^+$ lymphocytes by flow cytometry.

Sample Treatment: Samples were treated as described in section 6, except for the following:

Step 1:

1 volume of concentrated detergent solution was added to 5 volumes of fresh EDTA whole blood, followed by gentle mixing. Usually 100 μl of whole blood was treated with 20 μl of detergent solution. A comparison of detergents of various concentrations indicated that the best results were obtained using a combination of detergents such as TWEEN-20 with TRITON® X-100 or TRITON® X-100 with NONIDET® P40. Any of the three detergents alone was not as effective. The detergent treated sample (100 μl sample plus 20 μl concentrated detergent) yielded to a final combined detergent concentration of 2.5%. The optimal detergent solution for measuring both total CD4 and total CD 8 using the same concentrated detergent solution was 9% TRITON®-X100 and 6% NONIDET® P-40 (15% total in the concentrated detergent solution) which corresponded to 1.5% TRITON® X-100 and 1% NONIDET® P-40 (2.5% total) in the treated sample. In other experiments, the final concentration of the detergents in the treated sample was similarly effective over a range of at least 1–2% TRITON® X-100 combined with 1–1.5% NONIDET® P-40.

Other methods of lysis, solubolization or disruption of cells including hypotonic treatment with distilled water, sonication, or addition of detergent at lower final concentrations (e.g. one detergent at 1% concentration in the treated sample) were tested and found not effective.

Step 2:

After 5 minutes, 100 μl of treated sample was diluted with 400 μl of dilution buffer to yield a 1:5 dilution. Fifty μl of this diluted sample (about 10 μl of whole blood) was used for each assay well. The assay configuration allowed whole blood volumes of 5–25 μl to be measured, since the resulting values fell within the range of the standard curve. Blood volumes above or below these amounts yielded values that fell outside the range of the standard curve. The importance of step 2 is the dilution of the detergent concentration in the treated sample to prevent "stripping" in the following assay and loss of signal. Samples corresponding to 50 μl of whole blood performed poorly in the CD4 immunoassay because the resulting values were outside the assay range, and because the detergent concentration was disruptive to the antibody sandwich formation or stability.

Assay. Samples were stored at −70° C. prior to assay. The samples were assayed in the one-step sandwich immunoassay as described in section 6. Total CD4 values were determined from-a standard curve. Standards were soluble, recombinant CD4 antigen prepared by removing the transmembrane region of the CD4 gene, followed by expression of the truncated gene in mammalian cells and recovery of recombinant CD4 antigen in the supernatant of the cell culture (see International Patent Publications WO88/01304 and WO89/02922).

7.2. EXPERIMENTAL RESULTS

Experiment 5: A standard curve for the total CD4 antigen method was generated using culture supernatant containing recombinant CD4 receptor (see FIG. 5). For the assay configuration used, the standard range was determined to be 0 to 200 units/μl with a correlation coefficient of 0.999.

Experiment 6: Specificity of the assay for the CD4 antigen. Blood samples were drawn from 4 normal volunteers and treated as follows: A sample from each was analyzed for white blood cell count and differential (the percentage of WBCs that were lymphocytes; see the formula in Section 6.1.2). The rest of the sample was divided; one-half was depleted of CD4+ cells by absorption with anti-CD4 coated Dynabeads (Dynal, Inc. Great Neck, N.Y.) while the other half was untreated. The depleted and untreated samples were again divided and one fraction analyzed by flow cytometry while the other was treated using the total CD4 method. CD4 positive cell number was calculated from the white blood cell count, lymphocyte differential, and percentage of CD4 cells by flow cytometry using the formula described in Section 6.1.2. The comparison of CD4 positive cell number to total CD4 antigen is given in Table V.

TABLE V

Specificity of the Total CD4 Antigen Assay for CD4 Antigen

| | Untreated Fractions | | Depleted Fractions | |
|---|---|---|---|---|
| # | Flow Cytometry cells/μl | Total CD4 Antigen units/μl | Flow Cytometry cells/μl | Total CD4 Antigen units/μl |
| 1 | 71 | 320 | 0 | 7 |
| 2 | 934 | 445 | 0 | 11.5 |
| 3 | 1109 | 345 | 40 | 15 |
| 4 | 912 | 395 | 45 | 15 |

Both the flow cytometry and the total CD4 methods indicated the removal of CD4 positive cells from all depleted fractions indicating that the assays were specific for the CD4 receptor.

Experiment 7: Assay dilution and linearity. This study was done to further verify assay sensitivity. Whole blood samples from normal volunteers were collected in EDTA. A and a portion of each was depleted of CD4 positive cells to serve as the sample diluent in order to keep the sample matrix as normal as possible. Samples were prepared neat and at ½, ¼ and ⅛ dilutions with concentrated detergent; and run in the CD4 immunoassay. Table VI shows the results of this experiment on 6 different samples. Values are presented as raw data as run in the assay. The zero value represents the assay value obtained for the depleted portion used as sample diluent. This value is included in the calculations of expected values.

TABLE VI

Dilution and Linearity of Assay

| Sample | Dilution | Units Detected | Units Detected | Percent Recovery |
|---|---|---|---|---|
| 585 | Neat | 64 | 64 | 100 |
| | 1:2 | 35 | 35.5 | 99 |
| | 1:4 | 24 | 21 | 114 |
| | 1:8 | 14 | 14 | 100 |
| | 0 | 7 | | |
| 586 | Neat | 89 | 89 | 100 |
| | 1:2 | 58 | 51 | 114 |
| | 1:4 | 34 | 31 | 110 |
| | 1:8 | 22 | 21 | 105 |
| | 0 | 11.5 | | |
| 593 | Neat | 79 | 79 | 100 |
| | 1:2 | 38 | 41 | 91 |
| | 1:4 | 26 | 22 | 119 |
| | 1:8 | 22 | 24 | 92 |
| | 0 | 16 | | |
| 598 | Neat | 63 | 63 | 100 |
| | 1:2 | 40 | 39 | 103 |
| | 1:4 | 30 | 27 | 111 |
| | 1:8 | 26 | 21 | 124 |
| | 0 | 15 | | |
| 599 | Neat | 69 | 69 | 100 |
| | 1:2 | 36 | 42 | 86 |
| | 1:4 | 28 | 28 | 100 |

TABLE VI-continued

Dilution and Linearity of Assay

| Sample | Dilution | Units Detected | Units Detected | Percent Recovery |
|---|---|---|---|---|
| | 1:8 | 22 | 22 | 100 |
| | 0 | 15 | | |
| 600 | Neat | 65 | 65 | 100 |
| | 1:2 | 36 | 40 | 90 |
| | 1:4 | 27 | 27 | 100 |
| | 1:8 | 21 | 21 | 100 |
| | 0 | 15 | | |

These results indicate that normal whole blood samples dilute linearly in the assay. The assay background is <20 units. Neat normal samples fall in the middle of the assay range, so dilution of even 1:2 should be rarely necessary.

Experiment 8: Cell enumeration using the total CD4 method. This study confirmed that it was possible to enumerate CD4 positive cells in whole blood by the total CD4 method. Both flow cytometry and total CD4 antigen assays were run by Maryland Medical Laboratory on normal and abnormal blood specimens that were less than 24 hours old. Flow cytometry was performed on a Coulter Epics Flow Cytometer; the CD4 immunoassay was read using a Molecular Devices VMAX ELISA reader. Samples with low CD4 positive cell counts were selected from HIV positive specimens. Cells were dually stained with anti-CD4 and anti-CD2 antibodies in order to make sure that the cells counted by Flow were CD4 positive T cells. A total of 95 samples (46 normal and 49 abnormal) were assayed for white blood cell number, lymphocyte differential, and percent $CD2^+CD4^+$ cells by flow cytometry and for the amount of CD4 by the total CD4 antigen method. The number of $CD4^+$ T lymphocytes was calculated from the cell count, differential and flow data and compared to the data obtained from the total CD4 method by linear regression. The distribution of the two types of samples was:

46 Normals
   CD4+ T cell Number 500–1600 cells/$\mu$l
   total CD4 antigen 222–600 units/ml
49 Abnormals
   CD4+ T cell Number 1–690 cells/$\mu$l
   total CD4 antigen 48–295 units/ml The results of the linear regression analysis are shown in FIG. 6, where units/ml from the total CD4 antigen method are compared to cells/$\mu$l from the flow analysis. The slope of the line (0.26) and Y-intercept (89.7) define the linear regression curve equation Y=0.26X+89.7, where the total CD4 antigen units/ml is calculated to be 0.26 times the total number of cells/$\mu$l plus 89.7. The correlation coefficient for the comparison is 0.946, which indicates that enumeration of CD4 positive cells via the total CD4 antigen method is as reliable as the same enumeration by flow cytometry.

7.3. DISCUSSION

The quantitation of CD4 receptor protein in treated samples of whole blood has been shown to be equivalent to flow cytometry for the enumeration of CD4 positive T lymphocytes (r=0.946). For the configuration of the assay used, sensitivity is 100 units/ml or 50 cells/$\mu$l, which allows the total CD4 antigen method to be used over a wide range (50–1600 cells/$\mu$l) of samples. In the 95 samples tested, the possible presence of CD4 positive monocytes did not interfere with the assay results. Since only 10 $\mu$l of whole blood is needed per test, the total CD4 method will be useful for detecting $CD4^+$ T cells in samples that are difficult to obtain. The total CD4 method can be run in laboratories without access to flow cytometry. The method is simple and can be competed in less than 4 hours. Samples can be treated quickly and assayed immediately or treated and stored frozen for batch testing. Such batch testing of longitudinal patient samples following a course of treatment is not subject to the errors obtained with flow cytometry measurements where samples are run separately on different days. The detergent treatment step of the total CD4 method also provides the added benefit of inactivating enveloped viruses which increases operator safety.

8. EXAMPLE: ENUMERATION OF CD8 POSITIVE CELLS BY THE TOTAL CD8 METHOD

8.1. MATERIALS AND METHODS

Samples: Patient samples included 49 sero-positive HIV-infected individuals and 46 healthy adult volunteers with $CD8^+$ cell counts ranging from 28 to 2983 cells/$\mu$l.

Sample Treatment: Whole blood samples were prepared as described in Section 7, supra. Two hundred $\mu$l of concentrated detergent solution (9% TRITON® X-100 and 6% NONIDET® P-40) were added to 1 ml of whole blood. Following gentle mixing, the sample was diluted 1:5 (50 $\mu$l treated sample plus 200 $\mu$l diluent) with diluent before assay. Treated samples were stored at −70° C. prior to assay.

Assay. Total CD8 was measured in detergent treated whole blood in a CELLFREE® CD8 immunoassay (T cell Sciences, Inc.) using a one-step, three hour format. Briefly, each well of a 96 well microtiter plate was coated with 100 $\mu$l of the murine anti-CD8 coating antibody in phosphate-buffered saline overnight at 4° C. The coating buffer was removed and 300 $\mu$l of blocking buffer (0.5% casein, 0.008% NONIDET® P-40, 0.005% EDTA in PBS) were added per well and incubated for 2 hours at 37° C. After washing the wells three times with 400 $\mu$l of wash buffer (PBS, pH 7.4, with 0.05% Tween 20), 50 $\mu$l of horseradish peroxidase (HRP) conjugated murine monoclonal anti-human CD8 antibody (10% FCS, 0.025% thimerosal, 0.01% gentamicin, 0.05% tween in Tris Buffered Saline, TBS) were added to all wells except those used as blanks. Fifty $\mu$l of CD8 standard or treated whole blood was added to 200 $\mu$l of diluent (1% bovine serum albumin, phosphate buffered saline, 0.25% NONIDET® P-40 and 0.01% thimerosal) and 50 $\mu$l of this were added to the appropriate microtiter wells. The plate was covered with plate sealer and incubated for three hours at 20° C. with shaking at 150 rpms. After washing the plate as described above, 100 $\mu$l of OPD substrate were added to all the wells, and the plate was incubated at 20° C. for 30 minutes. Fifty $\mu$l of 2N $H_2SO_4$ were added to all wells to stop the reaction and absorbance was read at 490 nm. A standard curve (correlation>0.999; range 0–2300 units/$\mu$l; assay background <100 units) was constructed by plotting O.D. against the concentration of the standards. The concentration of total CD8 in the whole blood samples was then determined from the standard curve. Correlation coefficients were calculated using linear regression analysis.

Whole blood samples from normal and HIV-infected patients were assayed for absolute $CD8^+$ T-cells/mm$^3$ using the formula:

$$\text{Abs. } CD8^+ \text{ T-cells/mm}^3 = WBC \times \% \text{ lymphocyte} \times \% \ CD8^+ \text{ T cells.}$$

WBC (white blood cell count) was determined using a hemacytometer. % Lymphocyte was determined by a differential count, and %CD8+ T-cells were determined using the Ortho cytoflurograph II and Leu-2a (anti-CD8) fluorescein conjugated antibody (Becton Dickinson, Mountain View, Calif.)

8.2. EXPERIMENTAL RESULTS

Experiment 1. The specificity and linearity of the assay for CD8 were determined using similar depletion and dilution studies as described in Section 7. Total CD8 antigen values were obtained from whole blood of 43 normal and 43 HIV-infected, sero-positive individuals and compared to the total number of CD8+ T-cells/mm$^3$ of whole blood. Table VII summarizes the population statistics for the normal and abnormal samples by flow cytometry and the total CD8 method. The normal samples have a linear correlation of r=0.772 and the HIV+ samples have a linear correlation of r=0.718.

TABLE VII

| Samples | WBC* | % Lymph | % CD8* | # CD8* | Total CD8 units/ml |
|---|---|---|---|---|---|
| AVERAGE RANGE FOR 45 NORMAL PATIENT SAMPLES 26 patients were male ages ranged from 23–69 years 19 patients were female ages ranged from 18–65 years | | | | | |
| average | 6.48 | 31 | 23 | 483 | 949 |
| 2 STD | 3.04 | 10 | 14 | 181 | 343 |
| High | 10.2 | 41 | 42.3 | 898 | 2300+ |
| Low | 4.0 | 22 | 8.2 | 173 | 423 |
| AVERAGE RANGE FOR 49 HIV+ PATIENT SAMPLES 45 patients were male ages ranged from 24–65 years 4 patients were female ages ranged from 21–43 years | | | | | |
| average | 4.66 | 0.2 | 55 | 871 | 1368 |
| 2 STD | 5.76 | 26 | 28 | 1050 | 1244 |
| High | 19.9 | 61 | 7.5 | 2983 | 2300 |
| Low | 1.0 | 0.2 | 12.7 | 28 | 364 |

FIG. 7 demonstrates a statistically significant correlation between total CD8 antigen measured in the assay and the total number of CD8+ cells (r=0.75). In this study of 86 individuals, it was found that when total CD4 values were normal, so were total CD8 values. As CD4 values declined in HIV+ patients, the total CD8 values varied widely. Samples with low CD4 (<180 units/ml) and low CD8 values generally had low white blood cell counts as well. The HIV+ patients had some of the highest CD8 counts, perhaps to replace their diminished CD4+ T cells.

Experiment 2. Although it would be possible to enumerate CD8 positive cells using the total CD8 method of experiment 1 (r=0.75), this quantitation was not as accurate as the enumeration of CD4 positive cells by the total CD4 method (r=0.946). Since activation of CD8 positive cells results in the release of large amounts of soluble CD8 antigen, it is likely that the levels of sCD8 were affecting the correlation of total CD8 antigen levels with CD8 positive cell counts. To test this hypothesis, total CD8 antigen and soluble CD8 antigen were measured in 30 normal and 11 cancer (mainly melanoma and lymphoma) whole blood samples. Total CD8 antigen measurements were made as described above with the detergent treatment, dilution and immunoassay, and soluble CD8 levels were determined directly by immunoassay of plasma preparations. The same CD8 immunoassay was used for both the total CD8 antigen and soluble CD8 antigen. Since one volume of plasma (sample size) has twice the amount of plasma as an equivalent sized sample of whole blood, the soluble CD8 amounts in plasma were divided by two. The amount of cell associated CD8 (membrane bound plus cytoplasmic) was determined by subtracting the soluble levels of CD8 (divided by two) from the amount of total CD8 antigen. The results of this analysis are shown in FIG. 8.

Linear regression analysis of this data gave an improved correlation coefficient of 0.859 as compared to 0.75 for total CD8 antigen alone. Cell enumeration could be more accurately quantitated from the equation:

$$Y(cells/mm3)=1.1\times(units/ml\ total\ CD8\ antigen)+7.4.$$

8.3. DISCUSSION

As described herein, we have developed a total CD8 method that measures the level of total CD8 antigen in a patient sample. Whole blood samples were detergent treated, diluted, and assayed using a CD8 immunoassay in a one-step, three hour format. Total CD8 antigen values obtained in the total CD8 method correlated with total CD8+ T-cell number (r=0.75) in whole blood. A significant improvement in the ability to enumerate CD8+ cells in whole blood was found when the level of soluble CD8 antigen (released from activated cells) was subtracted from the level of total CD8 antigen (r=0.859). Monitoring the relationship of soluble and total antigen provided improved information on cell count and immune activation. Thus, the total CD8 assay alone, or in combination with other soluble or total marker assays, can be used to monitor the immune profile of patients.

9. EXAMPLE: ENUMERATION OF TCAR POSITIVE CELLS BY TOTAL TCR METHODS

Total TCAR β Experiments. An assay to detect total T cell antigen receptor (TCAR) β chain or total Vβ5 specific TCAR chain was performed using detergent treated whole blood samples in a total TCR method. Briefly, wells in a 96 well plate were coated with 5 μg/ml of coating antibodies which consisted of either a negative control antibody (δTCS1 which is specific for the Vδ5 region of the γδ T cell receptor), or W76 which recognizes the constant region of the β chain (Cβ) or a Vβ5 specific monoclonal antibody such as W112 (Tian et al., 1989, FASEB J. 3: A486 Abstr). A horseradish peroxidase conjugated (HRP)-βF1 antibody, which recognizes a different epitope of the β chain constant region (Cβ) than W76, was used as the detection 30 antibody. Whole blood lysates were prepared as described in Section 7, supra. The assay format was similar to that described in U.S. Pat. No. 4,845,026, issued Jul. 4, 1989 and entitled "Assay Systems for Detecting Cell-Free T Cell Antigen Receptor Related Molecules and Clinical Utilities of the Assays." In addition, a one-step, three hour format as described in Section 7, supra, was performed with similar results. Twenty-five μl of whole blood lysate was diluted in 75 μl of sample diluent for a starting dilution of 1:4. O.D. values from the negative control wells were subtracted from all values obtained (negative control wells using δTCS1 as the coating antibody averaged 0.10 and blank wells which had no antibody averaged 0.095).

The results of the total TCAR assay can be seen in FIG. 9. TCAR β chain was optimally detected at dilutions of 1:4 and 1:8. Vβ5 specific TCAR was detected at low levels (1:16 dilution) as well. Lower levels of Vβ5 were expected, since the Vβ5 positive subset of cells represents only a small portion of all β TCAR positive T cells. The assay demonstrated good specificity as the background O.D. was no higher when the control antibody δTCS1 was used as the coating antibody as compared to O.D.s obtained from blank wells which contain no coating antibody (0.100 and 0.095 respectively).

These data demonstrate that a total TCAR method can be used to detect the total amount of TCR β chain in a whole blood sample by using two monoclonal antibodies which recognize different regions of the constant region of the β chain. The total amount of β chain is an indication of the total amount of β positive T cells in the sample. Furthermore, specific subsets such as the Vβ5 family, which represent only 1–5% of the total TCAR β chains in normal blood, can be detected.

Total TCAR vδ1 Experiments. The treatment of samples was similar to that of section 7 with a concentrated detergent solution of 9% TRITON® X-100 and 6% NONIDET® P-40 in 1×PBS that was added to whole blood at a ratio of 200 μl concentrated detergent solution to 1 ml whole blood. Samples were then diluted 1:2 prior to immunoassay. The immunoassay procedure was similar to the CD4 or CD8 immunoassay except with antibody TCRδ1 as capture antibody and δTCS1 as detection antibody. The TCAR δ positive cell line PEER was used as a positive control. A standard curve was generated with the units arbitraily assigned based upon a PEER cell sample preparation stored at −70° C. and assigned a value of 20,000 units. The specificity of the assay for TCAR δ chain was determined using an antibody-affigel stripping procedure. Affigel 10 was coupled to either BSA, anti-CD8 antibody 4C9 (an isotype control antibody), δTCS1, TCRδ1, Vδ2 or Vγ2 at 1 mg/ml concentration. A 50/50 slurry was made of each sample. Three hundred μl of a detergent treated PEER cell sample was added to 50 μl of each antibody-affigel slurry. The sample/gels were incubated for 1 hour at 4° C. The samples were then centrifuged for 5 minutes at 10K. The supernatant fluid was removed and added to 50 μl more of the antibody-affigel slurries. The samples/gels were incubated for another hour at 4° C. This process was repeated for a total of three sample/affigel incubations. After the last centrifuge spin, the supernatants were removed and run in the assay as samples. The supernatants were not diluted 1:2 prior to assay, because the PEER sample was diluted 1:25 in sample diluent buffer before the antibody-affigel stripping. Samples that were not stripped with antibody-affigel were kept at 4° C. while the other samples were being stripped. The only two antibodies to completely strip the TCR δ reactivity from the samples were the TCAR δ chain specific antibodies δTCR1 and TCSδ1, indicating that the assay was specific for TCR δ chain. When 8 samples were run in the total TCAR δ chain method, total TCAR δ ranged from 55 to 108 units (FIG. 10). These all fell at the lower end of the standard curve.

The success of these total TCAR methods for measuring total β or total δ TCR antigen amounts can be extended to total Vα, total γδ, total αβ or to total Vγ, and related subset assay procedures as well. Detection of the total amount of the above β and δ antigens is useful in cell typing and in correlating specific V region expression to disease state or treatment outcome.

10. DEPOSIT OF HYBRIDOMAS

The following hybridoma cell lines, producing the indicated monoclonal antibody, have been deposited with the American Type Culture Collection, Rockville, Md., and have been assigned the listed accession numbers:

| Accession Hybridoma Number | Monoclonal Antibody | — |
| --- | --- | --- |
| Cell line 4C9 | 4C9 (anti-CD8) | HB 9340 |
| Cell line 5F4/7B12 | 5F4/7B12 (anti-CD8) | HB 9342 |
| Cell line 8F4 | 8F4 (anti-CD4) | HB 9843 |
| Cell line R2B7 | R2B7 (anti-CD4) | HB 9842 |
| Cell line 8A3.31 | 8A3.31 (βF1) | HB 9283 |
| Cell line δTCS1 | δTCAR3 = δTCS1 | HB 9578 |
| Cell line W112 | W112 (Vβ5) | HB 9927 |
| Cell line W4F.5B | W4F.5B (anti-cβ) | HB 9282 |
| Cell line 5A6.E9 | TCRδ1 | HB 9772 |

The present invention is not to be limited in scope by the cell lines deposited since the deposited embodiments are intended as single illustrations of one aspect of the invention and any cell lines which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various references are cited herein, the disclosures of which are incorporated by reference herein in their entireties.

What is claimed is:

1. A kit for determining the total amount of a leukocyte marker in a sample comprising:

(a) a concentrated non-ionic detergent solution: and (b) an immunological detection means specific for the leukocyte marker;

each in a suitable container.

2. The kit of claim 1 in which the concentrated non-ionic detergent solution comprises 9% TRITON® X-100 and 6% NONIDET® P-40.

3. The kit of claim 1 in which the immunological detection means comprises a capture antibody specific for the leukocyte marker and a detection antibody specific for the leukocyte marker for use in a sandwich immunoassay.

4. The kit of claim 1 which further comprises a standard comprising a known number of cells positive for the leukocyte marker.

5. The kit of claim 1 which comprises immunological detection means for more than one leukocyte marker.

* * * * *

UNITED STATES PATENT AND TRADEMARK OFFICE
CERTIFICATE OF CORRECTION

PATENT NO. : 5,811,525
DATED : September 22, 1998
INVENTOR(S) : Ritterhaus

It is certified that error appears in the above-indentified patent and that said Letters Patent is hereby corrected as shown below:

At col 1, in TABLE I, line 64, please delete "T40/251" and insert therefor --T40/25--;

At col 2, in TABLE I, line 55, please delete "CDS1" and insert therefor --CD51--;

At col 2, in TABLE I, line 62, please delete "Mel-14";

At col 3, in TABLE I, line 8, please delete "il" and insert therefor --11--;

At col 3, in TABLE I, line 21, please delete "international" and insert therefor --International--;

At col 5, line 66, please delete "T35" and insert therefore --T--.

At col 7, line 35, please delete "," after the word or;

UNITED STATES PATENT AND TRADEMARK OFFICE
CERTIFICATE OF CORRECTION

PATENT NO. : 5,811,525
DATED : September 22, 1998
INVENTOR(S) : Ritterhaus

It is certified that error appears in the above-indentified patent and that said Letters Patent is hereby corrected as shown below:

At col 7, line 65, please insert --.-- after the word disorder;

At col 7, line 65, please delete "significantly" and insert therefor --Significantly--;

At col 10, line 23, please delete "articular" and insert therefor --particular--;

At col 12, line 37, please delete "mab1" and insert therefor --mAb1--;

UNITED STATES PATENT AND TRADEMARK OFFICE
CERTIFICATE OF CORRECTION

PATENT NO. : 5,811,525
DATED     : September 22, 1998
INVENTOR(S) : Ritterhaus

It is certified that error appears in the above-identified patent and that said Letters Patent is hereby corrected as shown below:

At col 18, line 44, please delete "-" between the words include and the;

Signed and Sealed this

Second Day of March, 1999

Attest:

Attesting Officer

Q. TODD DICKINSON

Acting Commissioner of Patents and Trademarks